(12) United States Patent
Engelsher

(10) Patent No.: US 7,374,124 B2
(45) Date of Patent: May 20, 2008

(54) WINDING APPARATUS FOR BANDAGES AND RELATED METHODS

(76) Inventor: Helene Sue Engelsher, 101 Grohmans La., Plainview, NY (US) 11803

( * ) Notice: Subject to any disclaimer, the term of this patent is extended or adjusted under 35 U.S.C. 154(b) by 0 days.

(21) Appl. No.: 11/681,050

(22) Filed: Mar. 1, 2007

(65) Prior Publication Data

US 2007/0145179 A1    Jun. 28, 2007

Related U.S. Application Data

(63) Continuation-in-part of application No. PCT/US2004/039214, filed on Nov. 23, 2004.

(60) Provisional application No. 60/526,482, filed on Dec. 4, 2003.

(51) Int. Cl.
*B65H 75/48* (2006.01)

(52) U.S. Cl. .............................. 242/390.8; 242/532.6; 242/546

(58) Field of Classification Search ............. 242/532.6, 242/390, 390.8, 403, 404.2, 546
See application file for complete search history.

(56) References Cited

U.S. PATENT DOCUMENTS

| | | | |
|---|---|---|---|
| 437,554 A | 9/1890 | Bellamy | |
| 537,507 A | 4/1895 | Waldron | |
| 649,694 A | 5/1900 | Hunter | |
| 952,497 A | 3/1910 | Ballou | |
| 983,600 A | 2/1911 | Ballou | |
| 1,464,349 A | 8/1923 | Burg et al. | |
| 2,489,319 A | 11/1949 | Nave, Jr. et al. | |
| 2,571,175 A | 10/1951 | Williams et al. | |
| 3,113,742 A | 12/1963 | Bevan et al. | |
| 3,202,378 A | 8/1965 | Williamson | |
| 3,516,618 A | 6/1970 | Reinke | |
| 3,647,152 A | 3/1972 | Trewella | |
| 3,958,499 A | 5/1976 | Albee, Jr. | |
| 4,061,287 A | 12/1977 | Shakespeare | |
| 4,099,682 A | 7/1978 | Benuska | |
| 4,161,298 A | 7/1979 | Davis | |
| 4,834,079 A | 5/1989 | Benckhuijsen | |
| 4,852,822 A | 8/1989 | Brady | |
| 4,892,265 A | 1/1990 | Cox | |
| 4,911,156 A | 3/1990 | Libertucci | |
| 4,951,890 A | 8/1990 | Sossamon | |
| 4,974,398 A | 12/1990 | Kaski | |
| 5,524,843 A | 6/1996 | McCauley | |
| 5,533,689 A | 7/1996 | Chalfant | |
| 5,910,126 A | 6/1999 | Wilson et al. | |

(Continued)

*Primary Examiner*—William A Rivera
(74) *Attorney, Agent, or Firm*—Carter, DeLuca, Farrell & Schmidt, LLP.

(57) ABSTRACT

A portable, hand held winding apparatus, a kit, and a method of using the winding apparatus, for rolling up or winding elongate bandages and the like, are disclosed. The winding apparatus includes a hand held rotary drive device having a motor-driven rotatable connector that is adapted to operatively engage a connecting member, the rotatable connector defining an axis of rotation. The winding apparatus also includes a tensioning member supportable on the rotary drive device, the tensioning member including a tensioning arm extending in a direction substantially parallel to the rotational axis of the rotatable connector of the rotary drive device, the tensioning arm defining a slot therein. The tensioning member may further be configured to include a tensioning mechanism. The winding apparatus further includes a winding peg configured to receive a bandage thereabout and including a connecting member extending axially therefrom. The connecting member being operatively engagable with the rotatable connector of the rotary drive device.

24 Claims, 28 Drawing Sheets

U.S. PATENT DOCUMENTS

| | | | |
|---|---|---|---|
| 5,961,061 A * | 10/1999 | Stanley | 242/395 |
| 6,015,111 A | 1/2000 | Berke | |
| 6,276,627 B1 | 8/2001 | Brodock | |
| 6,286,779 B1 | 9/2001 | Devine | |
| 6,398,147 B1 | 6/2002 | Fredrickson | |
| 6,550,712 B1 | 4/2003 | Peterpaul | |
| 6,648,262 B1 | 11/2003 | Huffman | |
| 6,685,125 B1 | 2/2004 | Tucci | |
| 6,705,597 B1 | 3/2004 | Reilly et al. | |
| 2002/0088893 A1 | 7/2002 | Nichols | |
| 2003/0168546 A1 | 9/2003 | Bankston | |
| 2004/0016844 A1 | 1/2004 | Felts et al. | |
| 2004/0035973 A1 | 2/2004 | Henrion | |
| 2004/0108404 A1 | 6/2004 | Wiermaa | |

* cited by examiner

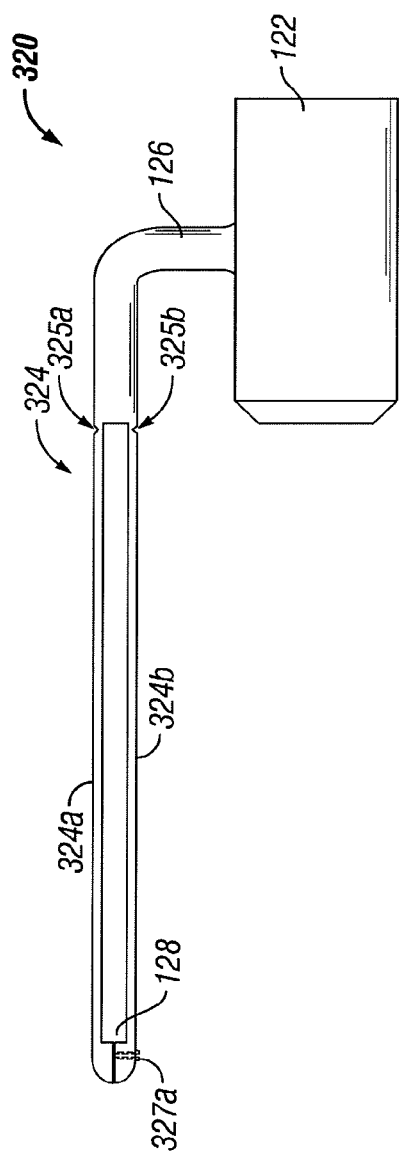
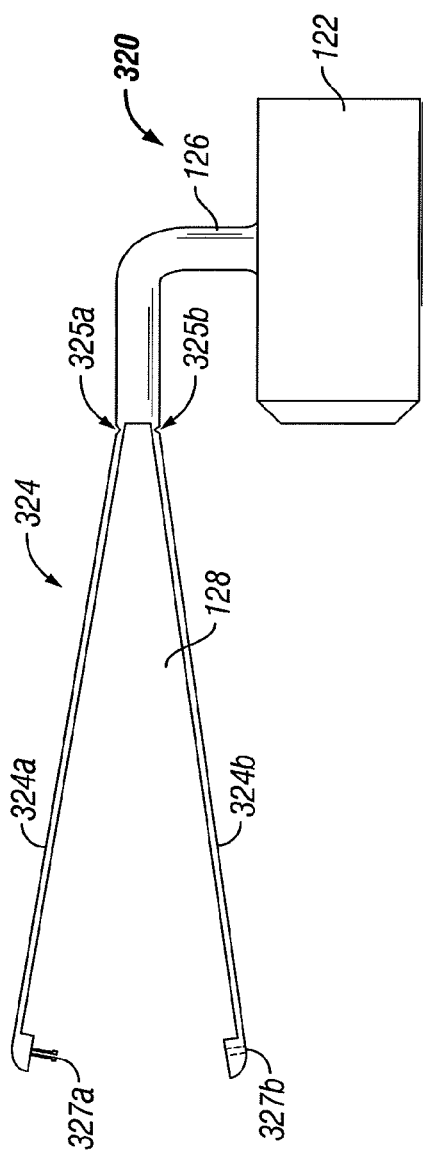
FIG. 10
FIG. 11

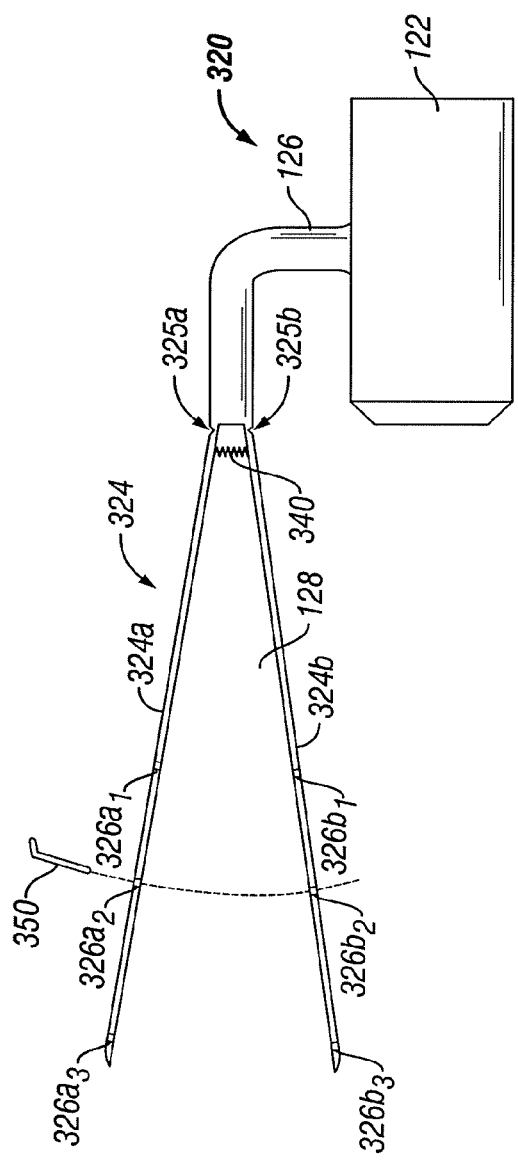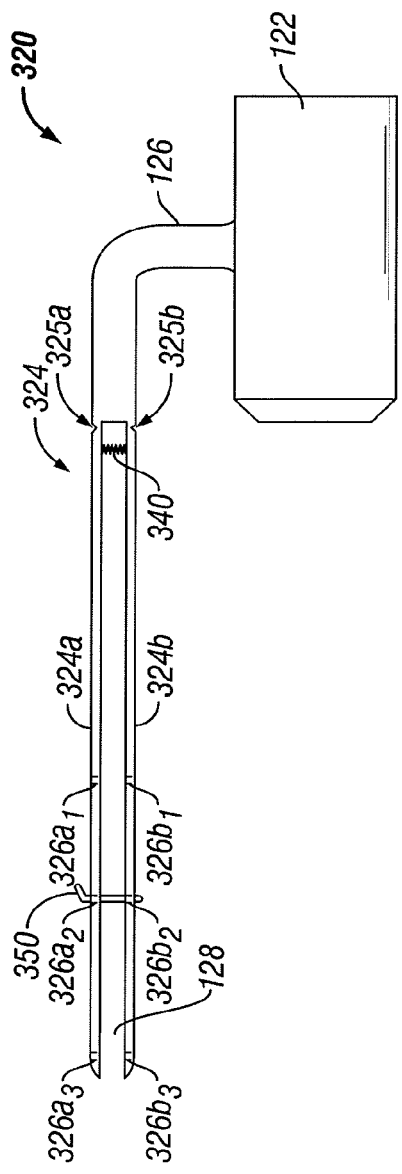
FIG. 12
FIG. 13

WINDING APPARATUS FOR BANDAGES AND RELATED METHODS

CROSS-REFERENCE TO RELATED APPLICATIONS

The present disclosure is a continuation in part of, and claims benefit of and priority to, PCT Patent Application No. PCT/US04/39214, filed Nov. 23, 2004, which claims benefit of and priority to U.S. Provisional Application Ser. No. 60/526,482, filed on Dec. 4, 2003, the entire contents of each are hereby incorporated by reference.

BACKGROUND

1. Technical Field

The present disclosure relates to apparatus and methods for winding and re-winding reusable bandages such as gauze, elastic compression bandages and cotton bandages and, more particularly, to machines, device and apparatus and methods for re-winding elongated leg wraps (i.e., polo-wraps, etc.) commonly used for wrapping the legs and/or ankles of horses.

2. Background of related Art

It has been a long standing practice for handlers of horses to use elongated bandages or the like to wrap the legs of horses in order to protect the horse's legs during certain activities. The bandages or "wraps" (i.e., polo-wraps) typically used for this purpose are relatively long strips of cloth material which may have a certain amount of resiliency, yieldability or stretch so that the bandage may be wrapped, in a spiral fashion, around a leg of a horse to fit snuggly over the irregular leg contour. Bandages used for this purpose are often about a few inches wide (e.g., 4 or 5 inches) and may be about several feet long (e.g., 8 feet) so as to furnish enough length for wrapping an adequate distance along the leg of the horse.

These bandages are reused many times. Accordingly, in order to properly and easily wrap a horses leg with these bandages it is preferred that the bandages be in a rolled condition (i.e., in a relatively uniformly wound cylindrical shape or roll). These bandages are applied to the horse's legs when the horse is standing. Thus, it is more practical and easier for the bandages to be in a rolled condition when they are wrapped on to the horse's leg.

Since it is preferred and practical for the bandages to be wrapped onto the horse's legs while initially in a rolled condition, a great deal of time and effort is devoted to the task of winding the bandages into a roll following each use thereof.

Typically and in practicality, bandages of this type may not be and are not wound into a cylindrical roll at a designated location or site. These bandages are usually kept in relatively close proximity to the stall where the particular horse with which they are used is stabled. Additionally, it is impractical to carry the bandages to a designated location for winding, especially when the bandages are applied to the horse's legs immediately before the horse is to be exercised in an integral step of the grooming sequence which must be carried out in the stall location.

Accordingly, a need exists for a winding device which overcomes the drawbacks mentioned above and which accomplishes the objects detailed herein.

It is, therefore, a primary object of the present disclosure to provide machines, device and/or apparatus for re-rolling relatively long, narrow bandages such as leg wraps or polo-wraps which overcomes the foregoing noted drawbacks.

In the achievement of this objective, the present disclosure provides a winding apparatus requiring no fixed installation or no attachment to a fixed structure, wherein the winding apparatus may be readily used at any location.

The present disclosure further provides a winding apparatus which may be operated with a single hand.

The present disclosure further provides a winding device which utilizes a winding peg which remains in the wound bandage following winding thereof and which facilitates application of the bandage to a horse's leg.

Additional objects and advantages of the present disclosure will be set forth in part in the description that follows, and in part will become apparent from the description or can be learned by practice of the present disclosure. The advantages of the present disclosure can be realized and obtained by the apparatus particularly pointed out in the appended claims.

BRIEF DESCRIPTION OF THE DRAWINGS

The foregoing summary, as well as the following detailed description will be better understood when read in conjunction with the appended figures. For the purpose of illustrating the present disclosure, a preferred embodiment is shown. It is understood, however, that the present disclosure is not limited to the precise arrangement and instrumentalities shown.

FIG. 10 is a front elevational view of a tensioning member according to a further embodiment of the present disclosure, shown in a closed condition;

FIG. 11 is a front elevational view of the tensioning member of FIG. 10 shown in an open condition;

FIG. 12 is a front elevational view of a tensioning member according to yet another embodiment of the present disclosure, shown in an open condition;

FIG. 13 is a front elevational view of the tensioning member of FIG. 12 shown in a closed condition;

DETAILED DESCRIPTION OF THE DRAWINGS

Figure 1:
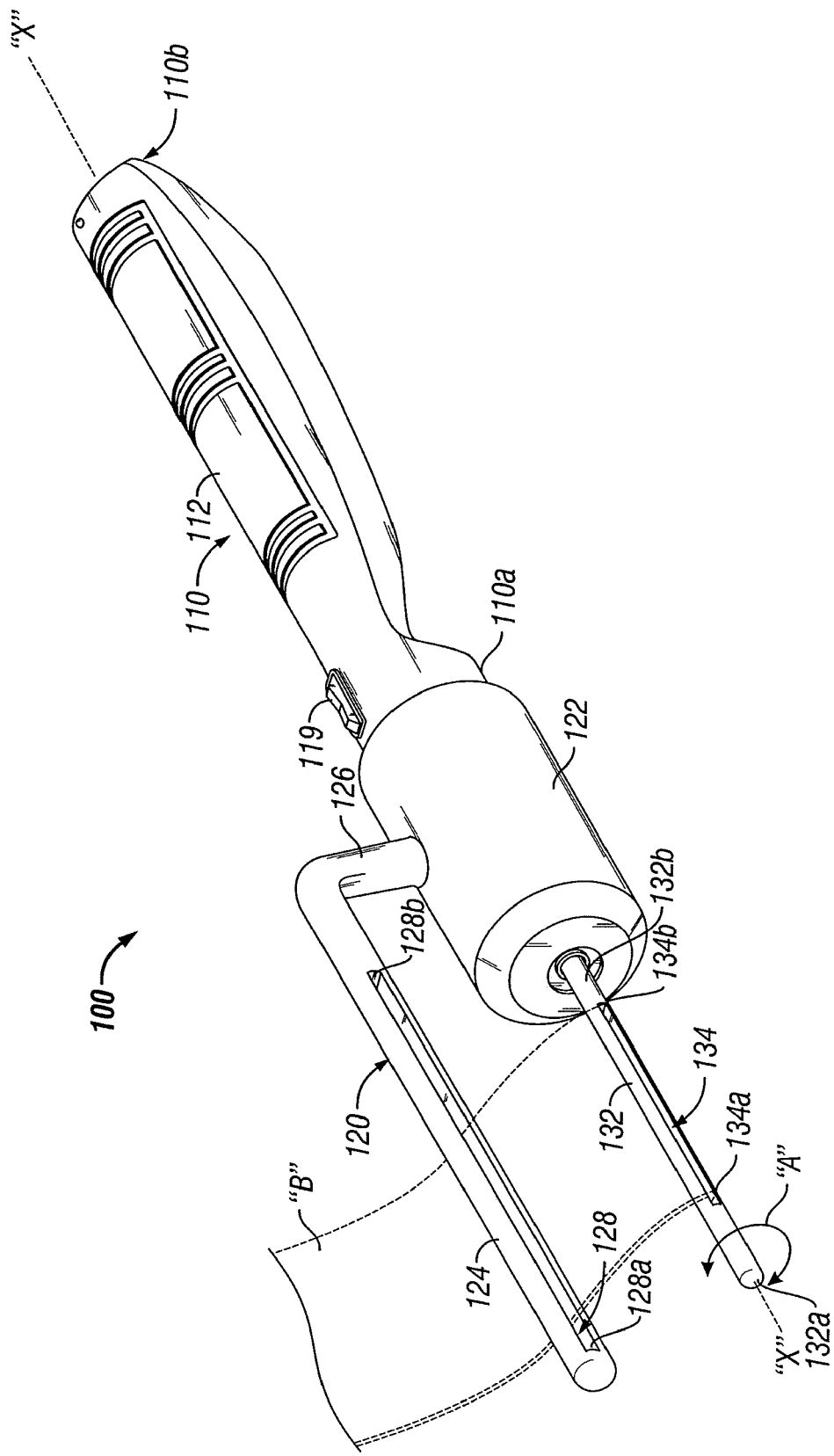
FIG. 1 is a perspective view of the winding apparatus according to an embodiment of the present disclosure, illustrating feeding of a bandage (shown in phantom) through a tension arm and onto a winding peg thereof.

Preferred embodiments of winding apparatus and methods in accordance with the present disclosure will now be described in detail with reference to the drawing figures wherein like reference numerals identify similar or identical structural elements. As shown in the drawings and described throughout the following description, as is traditional when referring to relative positioning on an object, the term "proximal" refers to the end of the apparatus which is closer to the user and the term "distal" refers to the end of the apparatus which is further from the user.

The various winding apparatus disclosed herein may be used to wind bandages for a myriad of reasons. For example, the winding apparatus may be used to wind bandages used in connection with the treatment of lymphedema and the like, as discussed in U.S. Pat. No. 6,286,779, the contents of which are incorporated by reference herein in its entirety. However, in the interest of clarity and for illustrative purposes only, the winding apparatus disclosed herein will relate to its use in winding polo-wraps or bandages and the like.

Figure 2:
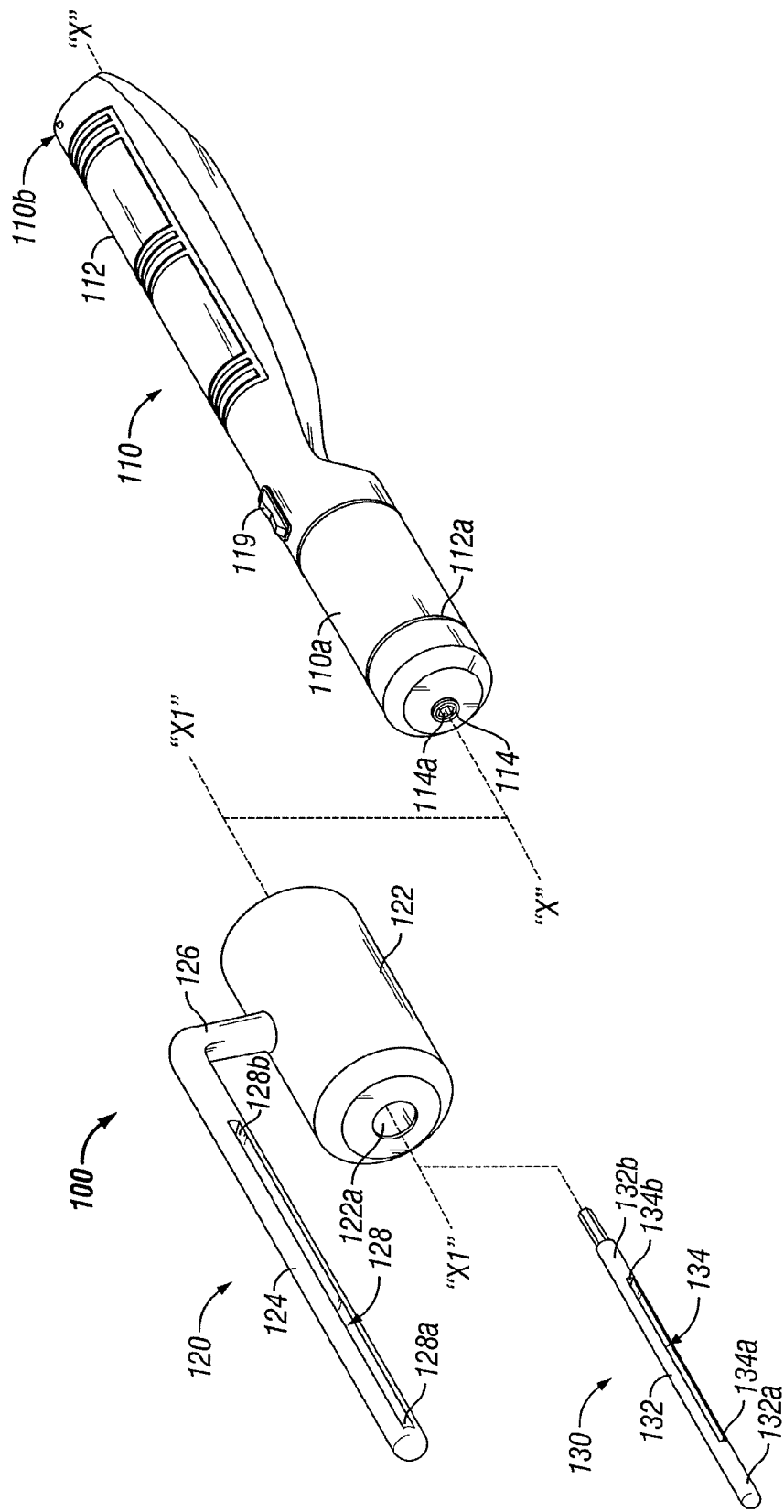
FIG. 2 is a perspective view, with parts separated, of the winding apparatus of FIG. 1.
Figure 3:
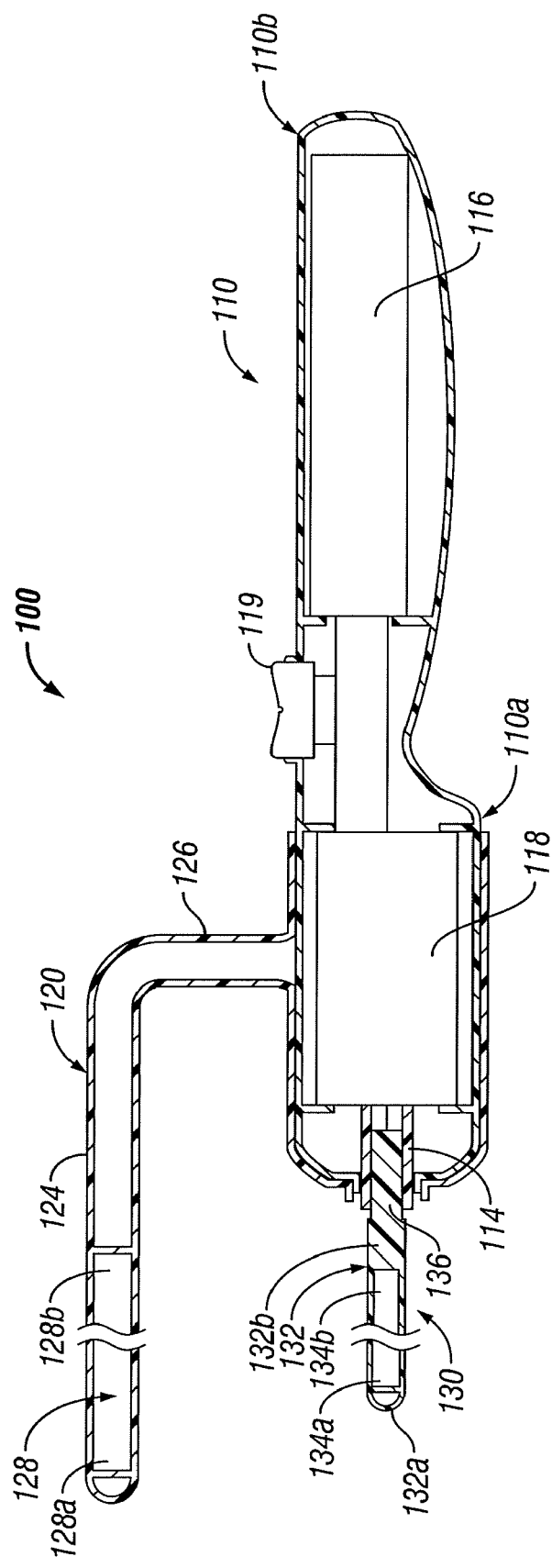
FIG. 3 is a schematic illustration of the winding apparatus of FIGS. 1 and 2, illustrating internal components thereof.

Referring to FIGS. 1-3, an illustrative embodiment of the presently disclosed winding apparatus is illustrated therein and generally designated as winding apparatus 100. Winding apparatus 100 includes a motorized or electric, hand-held, rotary drive device 110, such as for example, a powered screw driver tool or drill;, a tensioning member 120 selectively connectable to a distal end portion 110a of rotary drive device 110; and at least one winding peg 130 selectively connectable to a rotatably connector 114, here shown as a receptacle or chuck, provided at distal end portion 110a of rotary drive device 110.

As seen in FIGS. 1-3, rotary drive device 110 includes a housing 112 that contains the internal components of rotary drive device 110. Housing 112 may be constructed with a variety of materials including and not limited to, metal, plastics and the like. Housing 112 may be rigid and non-porous. Desirably, housing 112 may take the form of a baton and the like, however, other configurations are envisioned, such as, for example, a pistol-grip configuration. As illustrated in FIGS. 1-3, rotary drive device 110 may have a housing 112 having a substantially cylindrical body defining a proximal end gripping portion 110b formed into a shape that fits a user's hand, and a distal end portion 110a, axially aligned with proximal end portion 110b, and configured to selectively receive tensioning arm 120 and winding peg 130.

It is envisioned that distal end portion 110a may be angled with respect to proximal end portion 110b, for example, distal end portion 110a may be angled at approximately 60° or 90° with respect to proximal end portion 110b. It is further envisioned that distal end portion 110a may be pivotally connected to proximal end portion 110b and include a locking element for fixing the angular position of distal end portion 110a relative to proximal end portion 110b.

It is contemplated that housing 112 may include a grip (e.g., ridges formed in the surface of housing 112, a rubber sleeve or pads provided on or around at least portions of housing 112) to aid the user in gripping rotary drive device 110. Additionally, it may be necessary to access the internal components of rotary drive device 110. Accordingly, housing 112 may be constructing in two halves which may be joined together by snap-fit engagements, screws and the like.

As seen in FIG. 3, contained within housing 112 of rotary drive device 110 are the internal components thereof, which may include and are not limited to, a self-contained power supply 116 (e.g., batteries, either replaceable or rechargeable), a drive motor 118, preferably reversible, electrically connected to power supply 116, a chuck 114 rotatably supported in distal end portion 110a of rotary drive device 110 and operatively connected to the drive motor, and an actuation switch 119 electrically connected between the drive motor 118 and the power supply 116 to complete or interrupt a circuit therebetween. Desirably, drive motor 118 defines an axis of rotation "X" which extends substantially longitudinally along rotary drive device 110.

Chuck 114 is a generally rigid hollow cylinder including at least one planar surface 114a formed therein for engaging a complementary planar surface 136a formed in stem 136 of winding peg 130 to thereby transmit rotation to winding peg 130. In this manner, when the stem of winding peg 130 is inserted into chuck 114, the planar surface of the stem engages planar surface 114a of chuck 114. In use, with winding peg 130 connected to chuck 114, rotation of chuck 114 results in corresponding rotation of winding peg 130. It is envisioned that chuck 114 may include any number of planar surfaces, including and not limited to two, three, four, five, six, etc.

As seen in FIGS. 1-5, tensioning member 120 includes a cuff 122 preferably configured and adapted to selectively engage distal end portion 110a of rotary drive device 110. Cuff 122 defines a longitudinal axis "X1" extending therethrough. Tensioning member 120 further includes a tensioning arm 124 extending from cuff 122. Preferably, tensioning arm 124 extends in a direction substantially parallel to the longitudinal "X1" axis of cuff 122. Desirably, tensioning arm 124 may be offset from cuff 122 by a leg 126 extending radially from cuff 122.

As will be discussed in greater detail below, the length of leg 126 (i.e., the radial distance between the longitudinal "X1" axis of cuff 122 and that of tensioning arm 126) may be selected and/or varied depending on the length of bandage "B" to be wound on winding peg 130. For example, if a relatively shorter bandage "B" is to be wound on winding peg 130, then the length of leg 126 may be relatively smaller than the length of leg 126 if a relatively longer bandage "B" was to be wound on winding peg 130. Accordingly, the length of leg 126 should be selected such that as bandage "B" is being wound onto winding peg 130, the radius of the rolled-up bandage is less than the length of leg 126. It is envisioned and within the scope of the present disclosure that leg 126 may telescope. Thus, the length of leg 126 may be adjusted as needed for the particular length of bandage being rolled-up. By way of example only, a typical bandage "B" or polo-wrap used to wrap a horse's leg is approximately 6.0 feet (1.83 meters) to approximately 9.0 feet (2.74 meters) in length. As such, leg 126 may have a length approximately equal to 1.25 (3.18 cm) inches to thereby provide a sufficient distance between tensioning arm 124 and winding peg 130 to accommodate the size of the rolled-up bandage on winding peg 130.

As seen in FIGS. 1-5, tensioning arm 126 of tensioning member 120 includes an elongated slot 128 formed therein. Preferably, slot 128 is bounded at a distal end 128a and at a proximal end 128b thereof. In this manner, when bandage "B" is positioned therein, bandage "B" may not slide out of either distal end 128a or proximal end 128b of slot 128. In accordance with the present disclosure, slot 128 defines a plane which is substantially tangentially oriented with respect to the longitudinal "X1" axis of cuff 122 (i.e., perpendicular to a plane defines by the longitudinal "X1" axis of cuff 122 and the rotation "X" axis of drive motor 118).

As will be described in greater detail below, the orientation of slot 128 provides a degree of tensioning on bandage "B" as bandage "B" is being wound onto winding peg 130. The degree of tension transmitted to bandage "B" may be increased or decreased depending on several factors. For example, the tension transmitted to bandage "B" during winding may be decreased by widening or increasing a height of slot 128. Also, the tension transmitted to bandage "B" during winding may by decreased by angling the orientation of slot 128 relative to the plane defined by the longitudinal "X1" axis of cuff 122 and the rotation "X" axis of drive motor 118.

By way of example only, slot 128 of tensioning arm 124 may have an overall length of approximately 4.0 inches (10.16 cm) to approximately 7.0 inches (17.78 cm), and preferably, between approximately 5.25 inches (13.34 cm) to approximately 6.25 inches (15.88 cm). Slot 128 may also have a height of approximately 0.25 inches (0.64 cm), although other heights are envisioned, contemplated and within the scope of the present disclosure.

Figure 4:
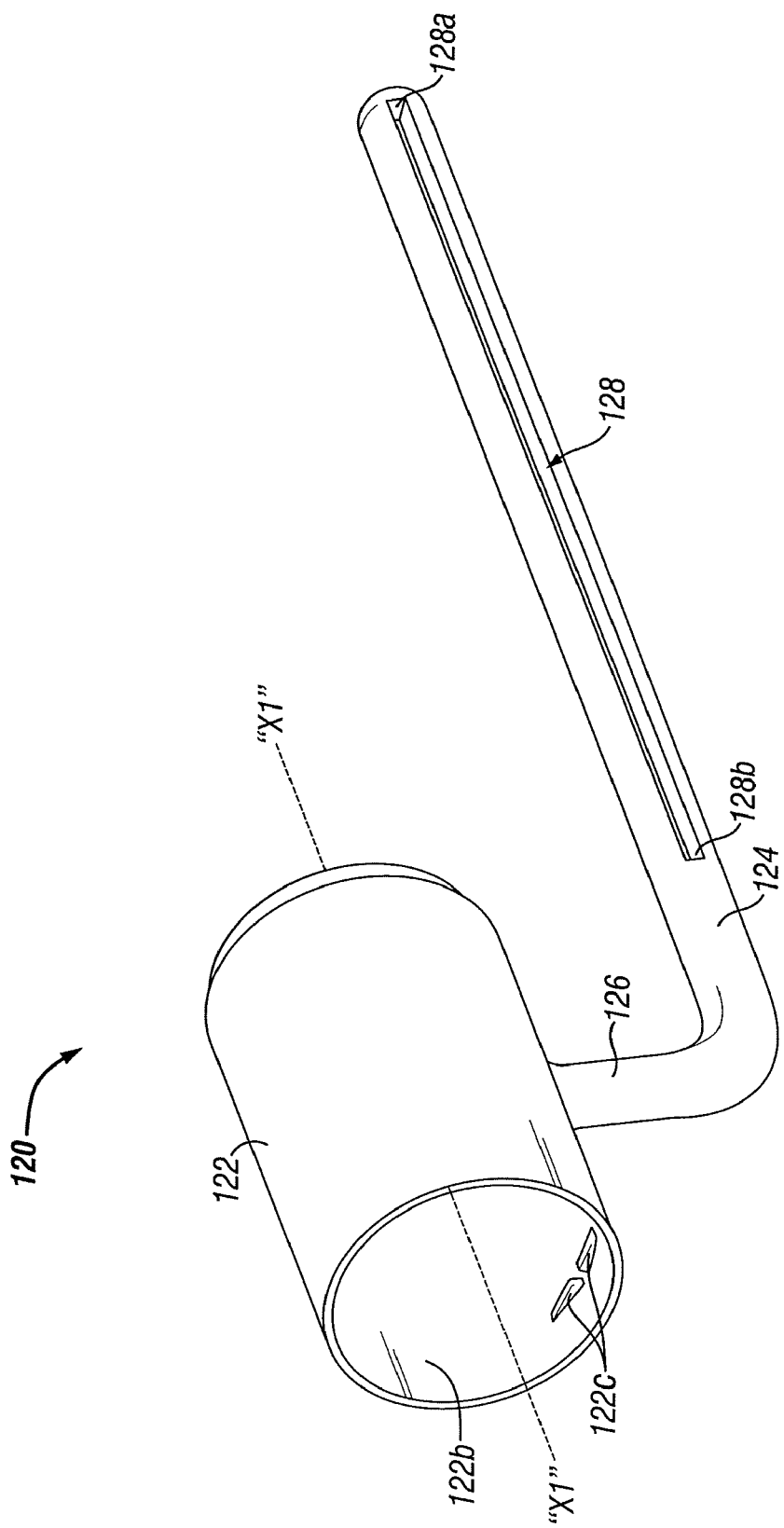
FIG. 4 is a perspective view of the tension arm of FIGS. 1-3.
Figure 5:
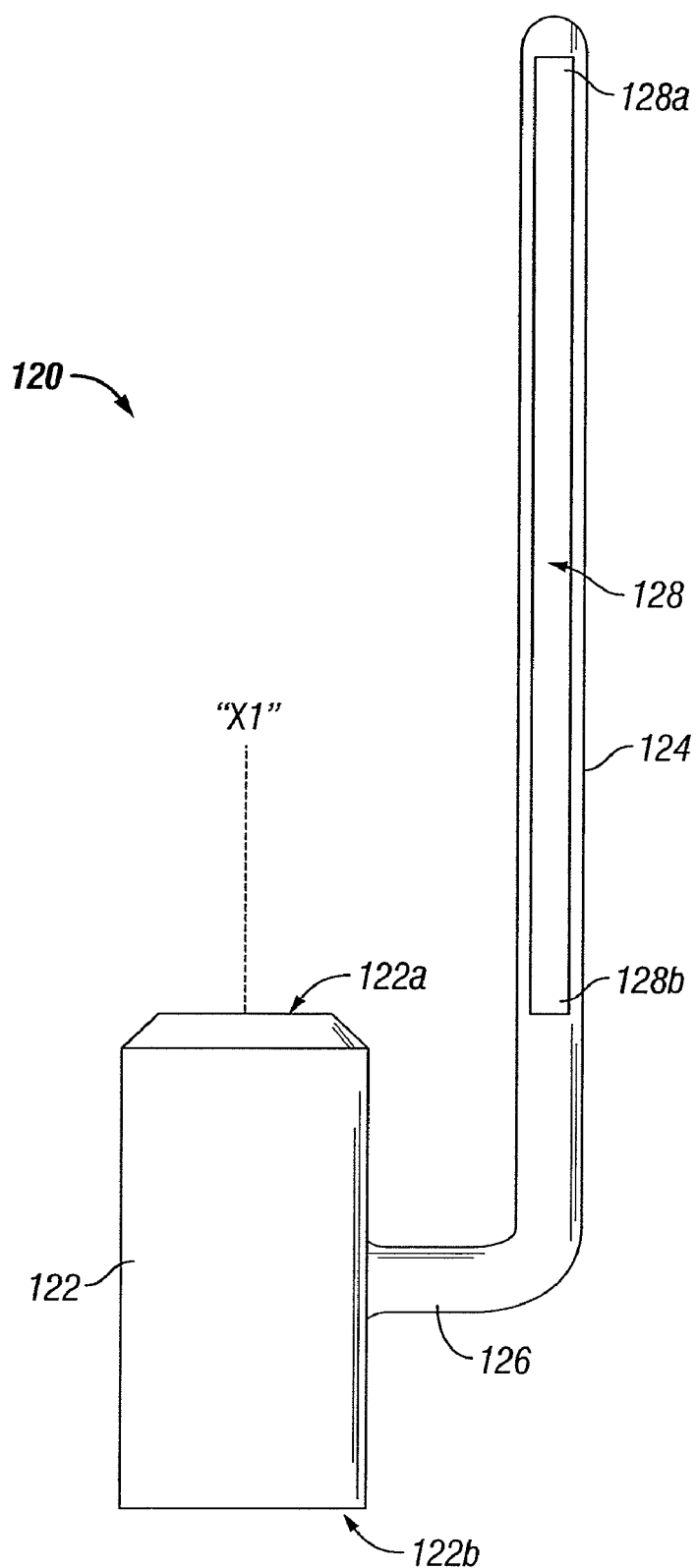
FIG. 5 is a side elevational view of the tension arm of FIGS. 1-4.
Figure 6:
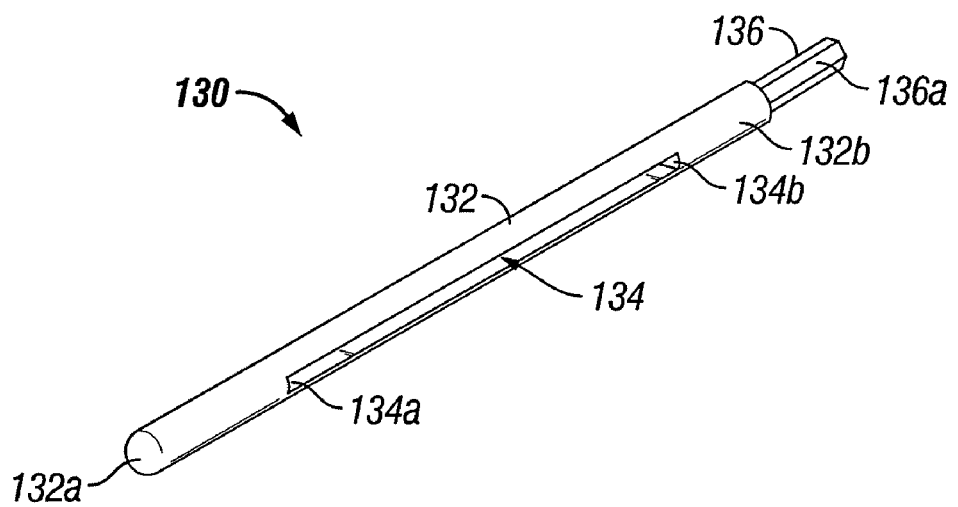
FIG. 6 is a perspective view of the winding peg of FIGS. 1-3.

Desirably, cuff 122 of tensioning member 120 includes an open proximal end 122b for receiving distal end portion 110a of rotary drive device 110 therein, and an aperture 122a formed in a distal end thereof through which chuck 114 of rotary drive device 110 may be accessed when tensioning member 120 is connected to rotary drive device 110. As seen in FIGS. 4 and 5, cuff 122 of tensioning member 120 further includes at least one projection 122c extending from an inner surface thereof. Preferably, projection 122c snap-fit engages corresponding complementary recesses 112a (see FIG. 2), here shown as an annular groove, formed in housing 112 of rotary drive device 110.

It is envisioned that the projection may be formed on the outer surface of housing 112 of rotary drive device 110 while the complementary recess may be formed in the inner surface of cuff 122 of tensioning member 120. It is further envisioned that cuff 122 of tensioning member 120 and distal end portion 110a of rotary drive device 110 may be configured and dimensioned such that cuff 122 of tensioning member 120 engages distal end portion 110a of rotary drive device 110 in a friction fit engagement. Additionally, cuff 122 of tensioning member 120 may be connected to distal end portion 110a of rotary drive device 110 by a bayonet-type inter-engaging structure (not shown), a screw-type engaging structure (not shown), or any other manner known by one having ordinary skill in the art.

Turning now to FIGS. 1-3, 6 and 7, winding peg 130 includes an elongate body portion 132 having a distal end portion 132a and a proximal end portion 132b. Winding peg 130 includes a slot 134 formed therein. Preferably, slot 134 is bounded or defined by a closed distal end 134a and a closed proximal end 134b. In this manner, when bandage "B" is positioned within slot 134 of winding peg 130, bandage "B" may not slide out of either distal end 132a or proximal end 132b of body portion 132.

Winding peg 130 includes a connecting member or stem 136 extending axially from proximal end portion 132b of body portion 132. Stem 136 is configured and adapted to be inserted into and/or be matingly received in chuck 114 of rotary drive device 110. In particular, stem 136 includes at least one planar surface 136a configured to operatively engage complementary planar surface 114a of chuck 114 and thereby receive the rotational forces created by chuck 114. In this manner, rotation of chuck 114 is a clockwise or counter-clockwise direction (as indicated by arrow "A" in FIG. 1).

While winding apparatus 100 has been shown as including a chuck 114 of rotary drive device 110 configured and adapted to receive stem 136 of winding peg 130 therein, it is envisioned and within the scope of the present disclosure for rotary drive device 110 to include a rotating stem (not shown) operatively connected to drive motor 118 and extending therefrom, and a winging peg 130 including a recess formed therein for engaging the stem of rotary drive device 110.

As seen in FIG. 1, when winding peg 130 is connected to rotary drive device 110, winding peg 130 is substantially aligned with the rotational "X" axis. Additionally, when winding peg 130 and tensioning member 120 are connected to rotary drive device 110, as seen in FIG. 1, winding peg 130 is substantially parallel with tensioning arm 124 of tensioning member 120.

By way of example only, slot 134 of winding peg 130 may have an overall length of approximately 1 inch (2.54 cm) to approximately 7.0 inches (17.78 cm), preferably between approximately 1.75 inches (4.45 cm) to approximately 5.25 inches (13.34 cm), and most preferably, approximately 2.25 inches (5.72 cm). Slot 134 of winding peg 130 may also have a height of approximately 0.125 inches (0.32 cm), although other heights are envisioned, contemplated and within the scope of the present disclosure. Slot 134 of winding peg 130 is dimensioned to receive a tab "T" (see FIG. 7) formed at one end of bandage "B", therein.

Figure 7:
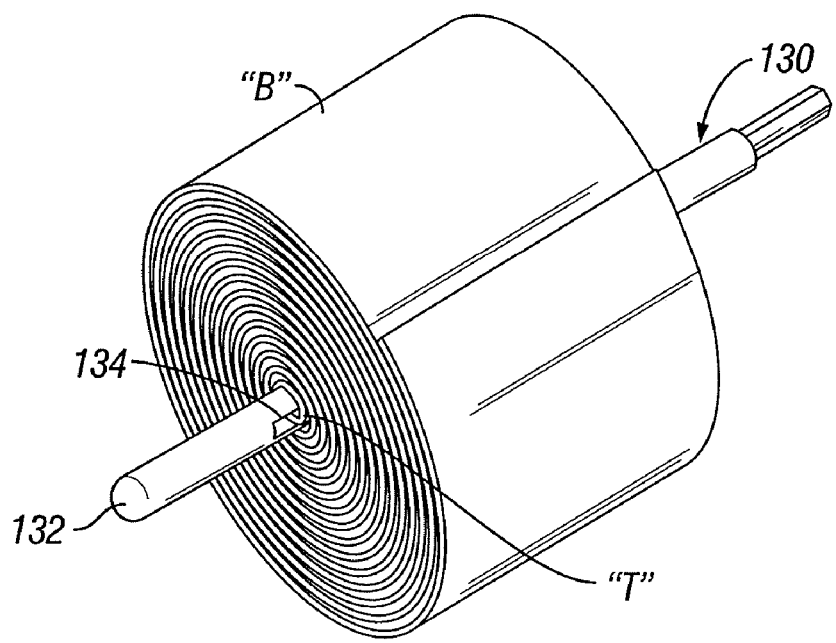
FIG. 7 is a perspective view of the winding peg of FIG. 6 including a bandage wound thereon.

As seen in FIG. 7, with tab "T" of bandage "B" inserted into slot 134 of winding peg 130, winding peg 130 has been wound in order to roll-up bandage "B" thereon and to thereby form bandage "B" into a cylinder, drum or the like. In accordance with the present disclosure, since slot 134 is bound between closed distal end 134*a* and closed proximal end 134*b* of winding peg 130, bandage "B" may not slide out of either distal end 132*a* or proximal end 132*b* of body portion 132.

With reference to FIGS. 1 and 7, a method of using winding apparatus 100, according to the present disclosure, is shown and described. Initially, tensioning member 120 and winding peg 130 are connected to rotary drive device 110 in the manner described above. In particular, distal end portion 110*a* of rotary drive device 110 is inserted into open proximal end 122*b*, preferably until projection 122*c* extending from the inner surface of cuff 122 snap-fit engages complementary recess 112*a* formed in the outer surface of housing 112. Also, stem 136 of winding peg 130 is inserted, through aperture 122*a* formed in the distal end of cuff 122 of tensioning member 120, and into chuck 114 of rotary drive device 110. Preferably, planar surface 136*a* of stem 136 engages complementary planar surface 114*a* of chuck 114. In this manner, as will be described in greater detail below, rotation of chuck 114 results in corresponding rotation of winding peg 130.

With tensioning member 120 and winding peg 130 connected to rotary drive device 110, an end (e.g., tab "T") of a polo-wrap or bandage "B" is threaded through slot 128 of tensioning member 120 and through or into slot 134 of winding peg 130 (see FIG. 1). With tab "T" of bandage "B" inserted through slot 128 of tensioning member 120 and into slot 134 of winding peg 130, the operator may hold winding apparatus 100 in one hand and depresses switch 119 to energize drive motor 118. Drive motor 118 rotates chuck 114 which, in turn, rotates winding peg 130 in the direction of arrow "A".

As winding peg 130 is rotated, bandage "B" is pulled through slot 128 of tensioning member 120 and wound onto winding peg 130. During winding of bandage "B" onto winding peg 130, tensioning arm 124 of tensioning member 120 maintains bandage "B" straight and taut or in tension. Rotary drive device 110 of winding apparatus 100 is operated until bandage "B" is entirely wound onto winding peg 130 (see FIG. 7). If needed, rotation of chuck 114 of rotary drive device 110 may be reversed so as to unwind a portion of bandage "B" which may contain dirt/debris or the like in order to remove the dirt/debris therefrom.

In operation, since slot 128 of tensioning arm 124 and slot 134 of winding peg 130 are closed at their respective distal end proximal ends, bandage "B" is prevented from sliding out of slot 128 of tensioning arm 124 and slot 134 of winding peg 130, as bandage "B" is being wound onto winding peg 130. Following winding of bandage "B" onto winding peg 130, the user removes (i.e., disconnects or uncouples) winding peg 130, including the rolled-up bandage "B", from rotary drive device 110.

Desirably, the free end of rolled-up bandage "B" is held against the remainder of rolled-up bandage "B" by any number of methods, including, and not limited to, tucking the free end of bandage "B" between adjacent layers of rolled bandage "B"; pinning the free end of bandage "B" against the rolled-up portion of bandage "B"; using a tie or elastic band around rolled-up bandage "B"; and stretching an elastic band from stem 136 of winding peg 130, across rolled-up bandage "B", and onto distal end portion 132*a*.

With reference to FIG. 7, since distal end 134*a* of slot 134 of winding peg 130 is closed, rolled-up bandage "B" may not be removed from winding peg 130 without un-rolling bandage "B" from winding peg 130. In other words, it is intended that winding peg 130 remains at the center of rolled-up bandage "B" until it is removed at the time bandage "B" is wrapped around the horse's leg.

Following removal of the rolled-up bandage "B" and winding peg 130, the rolled-up bandage "B" may be neatly stored on a shelf, in a basket, box or bin, in a bag, in a drawer, or on a peg board including a plurality of holes formed therein for receiving stem 136 of winding peg 130. Winding peg 130 may be used repeatedly as needed.

Following winding of a first bandage "B" onto a first winding peg 130, a second winding peg may be attached to rotary drive device 110 and a second bandage may be wound onto the second winding peg in the same manner as discussed above for the winding of the first bandage "B".

Desirably, tensioning member 120 and/or winding peg 130 are fabricated from a plastic or resin material. However, it is envisioned and within the scope of the present disclosure that tensioning member 120 and/or winding peg 130 may be fabricated from any material suitable for accomplishing the operations described above, such as, for example, metal (e.g., stainless steel, aluminum, etc.), wood, and the like.

Figure 8:
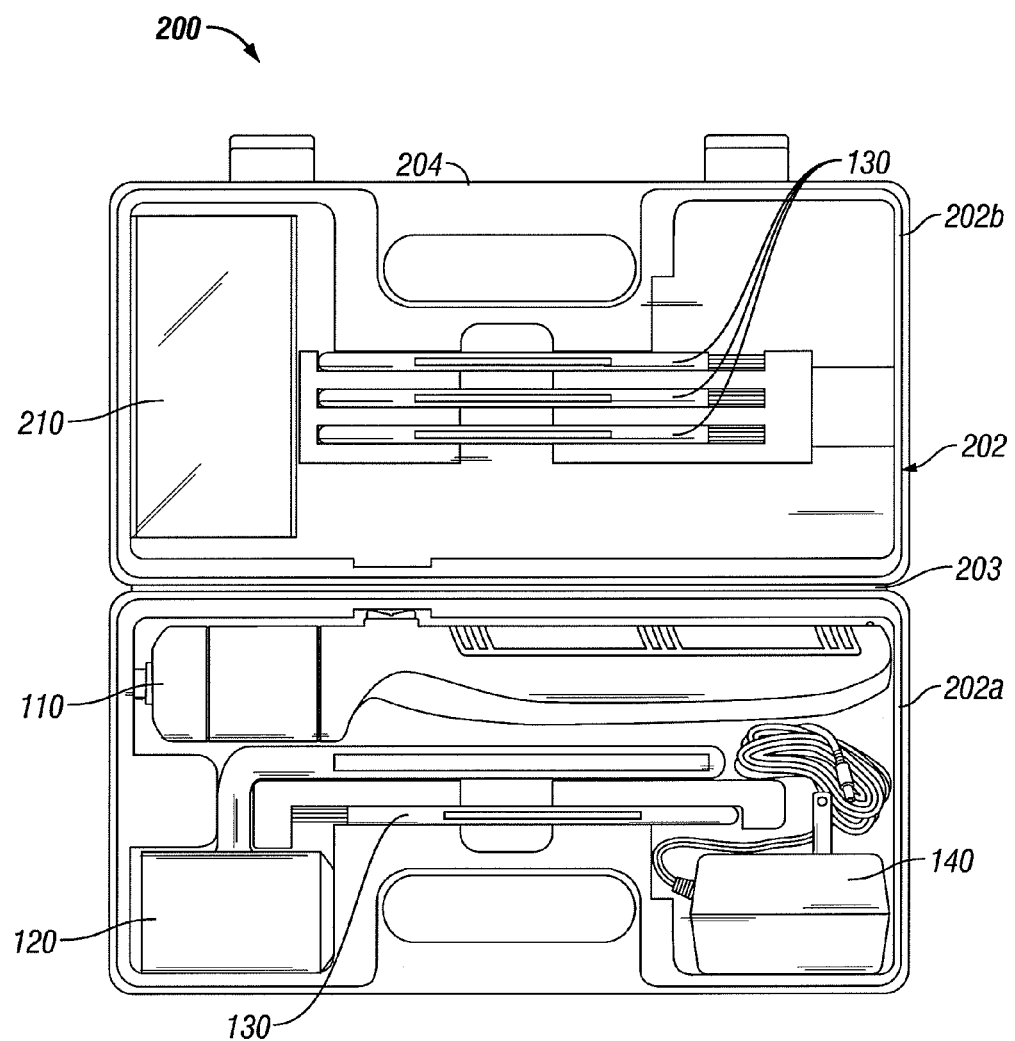
FIG. 8 is a plan view of a one illustrative embodiment of a kit including the winding apparatus of FIGS. 1-3.

Turning now to FIG. 8, winding apparatus 100 may be included in a polo-wrap or bandage rolling kit 200. Kit 200 may include a case 202 having a bottom case portion 202*a* and a lid or top case portion 202*b* hingedly connected to bottom case portion 202*a*. Desirably, case 202 may include a handle 204 provided or formed therewith.

Case 202 of kit 200 is configured and adapted to contain at least some of the following components or elements therein, including and not limited to: a rotary drive device 110, a tensioning member 120, and a plurality of winding pegs 130. Additionally, kit 200 may include instructions 210 describing and illustrating methods of using winding apparatus 100.

It is envisioned that rotary drive device 110 may be rechargeable. Accordingly, kit 200 may include a re-charger 140 which may be electrically connected to power supply 116 of rotary drive device 110 or to which power supply 116 may be electrically connected following removal of power supply 116 from housing 112 of rotary drive device 110. Alternatively, kit 200 may include a power adapter which may be electrically connected to rotary drive device 110 and provide power to drive motor 118.

Case 202 may be fabricated from molded plastic and the like and include designated regions configured and dimensioned to receive the specific components or elements of kit 200 identified above. Preferably, these designated regions may be configured to snap-fit engage the specific components of kit 200 identified above.

While several particular embodiments of winding apparatus 100 have been illustrated and described, it will also be apparent that various modifications may be made without departing from the spirit and scope of the present disclosure.

For example, it is envisioned that leg 126 may be fixedly attached to and/or integrally formed with or extending from housing 112 of rotary drive device 110. Accordingly, leg 126 and tensioning arm 124 may be formed as part of housing 112. In this manner, rotary drive device 110 may be constructed as a unitary element with leg 126 and tensioning arm 124 extending from housing 112 of rotary drive device. Alternatively, as will be described in greater detail below, tensioning member 120 may be modular, including a discrete tensioning arm 124, a discrete leg 126, and optionally a discrete cuff 122. It is also envisioned that leg 126 of tensioning member 120 may include a coupling element for engagement with a complimentary coupling element formed in housing 112 of rotary drive device 110 or in cuff 122.

It is further envisioned that tensioning arms 124 may be selectively connectable to leg 126 and that leg 126 may be selectively connectable to cuff 122 or housing 112. Accordingly, legs of varying length may be connected to cuff 122 or housing 112 depending on the length of polo-wrap or bandage "B" that is to be wound onto winding peg 130.

It is envisioned that winding peg 130 has a diameter of approximately 0.75 inches (1.91 cm). However, it is envisioned that winding peg 130 may have a larger or smaller diameter depending on the particular material of construction of winding peg 130, and depending on the particular winding characteristics desired for bandage "B".

Additionally, it is envisioned that drive motor 118 may be powered by power supply 116 and/or by an external power adapter such as an AC adapter, a DC power jack, a vehicle cigarette lighter adapter, and the like. It is envisioned that power supply 116 may be replaceable (i.e., power supply 116 may be removed from housing 112 of rotary drive device 110 and replaced with another power supply).

Figure 9:
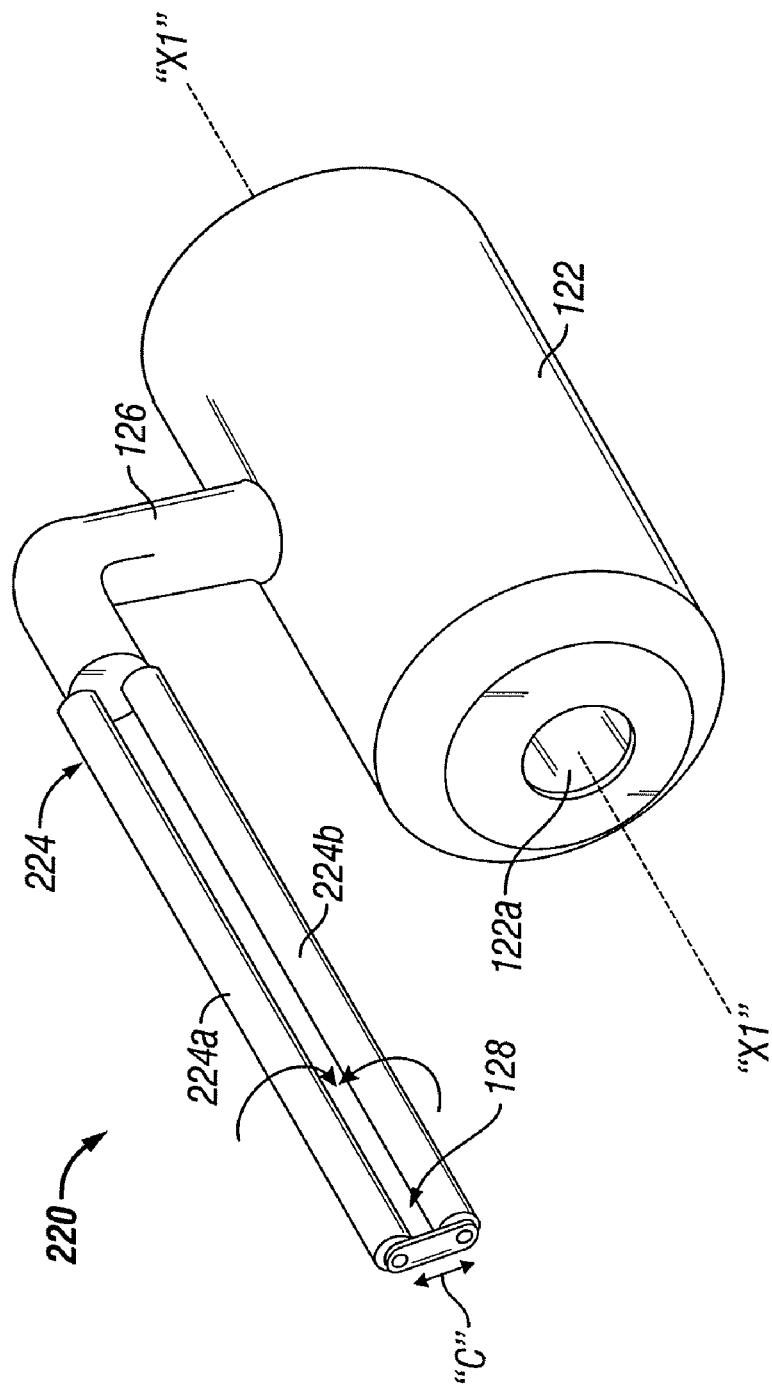
FIG. 9 is a perspective view of a tensioning member according to another embodiment of the present disclosure.

Turning now to FIG. 9, an alternate embodiment of a tensioning member for use with rotary drive device 110 is generally designated as 220. Tensioning member 220 is substantially similar to tensioning member 120 and will only be discussed in detail to the extent necessary to identify differences in construction and operation.

As seen in FIG. 9, tensioning member 220 includes a tensioning arm 224 operatively connected to leg 126. Tensioning arm 224 includes a pair of parallel spaced apart rollers 224a, 224b defining slot 128 therebetween. A distal end of rollers 224a, 224b are connected to one another by a bracket 229, which also functions to close off slot 128 and thereby prevent bandage "B" from escaping or sliding out of slot 128.

Desirably, it is envisioned that rollers 224a, 224b may be separated and approximated relative to one another, as indicated by arrow "C", in order to adjust the size or height of slot 128. For example, the height of slot 128 may be increased or decreased in order to increase or decrease the tension exerted on bandage "B" which is being fed therethrough.

Rollers 224a, 224b tend to reduce the wear and sliding friction on bandage "B" as bandage "B" is being pulled through slot 128. It is envisioned that rollers 224a, 224b may be fabricated from metal and/or plastic.

Rollers 224a, 224b define respective rotational axes "X2a, X2b". As mentioned above, the rotational "X2a, X2b" axes of rollers 224a, 224b are preferably parallel to the longitudinal "X1" axis of cuff 122. Desirably, rollers 224a, 224b are oriented such that the rotational "X2a, X2b" axes thereof are in a plane extending radially through the longitudinal "X1" axis of cuff 122. If is envisioned that rollers 224a, 224b may be oriented such that the rotational "X2a, X2b" axes thereof are in a plane which is angled with respect to the plane extending radially through the longitudinal "X1" axis of cuff 122, such as, for example, in a plane which is perpendicular to the plane extending radially through the longitudinal "X1" axis of cuff 122.

Turning now to FIGS. 10 and 11, an alternate embodiment of a tensioning member for use with rotary drive device 110 is generally designated as 320. Tensioning member 320 is substantially similar to tensioning member 120 and will only be discussed in detail to the extent necessary to identify differences in construction and operation.

As seen in FIGS. 10 and 11, tensioning member 320 includes a tensioning arm 324 operatively connected to leg 126. Tensioning arm 324 includes a pair of parallel spaced apart fingers 324a, 324b defining a slot 128 therebetween when in the closed position. Each finger 324a, 324b includes a hinge 325a, 325b formed or provided at or near a proximal end thereof. Preferably, hinges 325a, 325b are living hinges, however, other hinges known by one skilled in the art may be used. Hinges 325a, 325b enable fingers 324a, 324b to move from a closed condition shown in FIG. 10, wherein fingers 324a, 324b are substantially parallel to one another and slot 128 is closed, to an open condition shown in FIG. 11, wherein fingers 324a, 324b are angularly spaced from one another and slot 128 is open.

Tensioning member 320 further includes a locking element 327a configured and adapted to selectively secure or lock distal end 323a of finger 324a with distal end 323b of finger 324b. Locking element 327a further maintains slot 128 closed during winding of bandage "B" onto winding peg 130. Desirably, locking element 137a extends from distal end 323a of finger 324a and snap-fit engages a recess or aperture 137b (shown in phantom in FIG. 11) formed in distal end 323b of finger 324b.

Having a tensioning arm 324 which is capable of being opened enables bandage "B" to be more easily inserted into slot 128. For example, with tensioning arm 324 open, bandage "B" may be inserted into slot 128 by sliding bandage "B" side ways into slot 128 through open end 128c (see FIG. 11). With bandage "B" positioned in slot 128, first and second fingers 324a, 324b are approximated and distal ends 323a, 323b locked closed thereby preventing bandage "B" from sliding out of the end of tensioning arm during winding of bandage "B" onto winding peg 130.

Locking element 137a in combination with aperture 137b may be replaced by any element or feature which allows selective opening and closing of tensioning arm 324. For example, such features may include and are not limited to, a latch formed on one finger and a button formed on the other finger, a tie, a snap, etc.

Turning now to FIGS. 12 and 13, an alternate embodiment of a tensioning member for use with rotary drive device 110 is generally designated as 420. Tensioning member 420 is substantially similar to tensioning member 320 and will only be discussed in detail to the extent necessary to identify differences in construction and operation.

As seen in FIGS. 12 and 13, tensioning member 320 includes a biasing element 340 disposed between fingers 324a, 324b. Desirably, biasing element 340 is located near a proximal end of slot 128, however, it is envisioned that biasing member 340 may be located near a distal end of slot 128. As seen in FIG. 12, biasing element 340 functions to maintain fingers 324a, 324b spaced apart from one another (i.e., in an open condition).

Each finger 324a, 324b includes a series of through-holes formed therein. Desirably, finger 324a includes a series of through-holes 326a₁-326a₃ formed near a distal end thereof, and finger 324b includes a series of through-holes 326b₁-326b₃ formed near a distal end thereof and in registration with through-holes 326a₁-326a₃ of finger 324a when fingers 324a, 324b are in a closed condition.

It is contemplated that first through-holes 326a₁-326b₁ are spaced approximately 4.5 inches (11.43 cm) from a proximal-most end of slot 128, second through-holes 326a₂, 326b₂ are spaced approximately 5.5 inches (13.97 cm) from the proximal-most end of slot 128, and third through-holes 326a₃-326b₃ are spaced approximately 6.5 inches (16.51 cm) from the proximal-most end of slot 128.

A locking element or pin 350 (e.g., an L-pin, a cotter pin, etc.) is provided and is configured and dimensioned for insertion into respective through-holes 326a₁-326a₃ and 326b₁-326b₃ in order to maintain fingers 324a, 324b closed. Depending of the size or width of bandage "B" being wound by apparatus 100, pin 350 is inserted into particular through-holes 326a₁-326a₃ and 326b₁-326b₃ in order to set the width of slot 128. For example, for bandages "B" having a width less than approximately 4.5 inches, it is desirable to insert pin 350 into first through-holes 326a₁, 326b₁, for bandages "B" having a width less than approximately 5.5 inches, it is desirable to insert pin 350 into second through-holes 326a₂, 326b₂, and for bandages "B" having a width less than approximately 6.5 inches, it is desirable to insert pin 350 into second through-holes 326a₃, 326b₃.

Essentially, pin 350 functions to close the distal end of slot 128 and prevent bandage "B" from sliding out of the distal end of slot 128 during the winding procedure. Desirably, pin 350 may be tethered to tensioning member 320. Pin 350 may include a distal end which is slightly larger than the dimension of through-holes 326a₁-326a₃ and 326b₁-326b₃ thereby allowing pin 350 to snap-fit engage 326a₁-326a₃ and 326b₁-326b₃.

It is contemplated that through-holes 326a₁-326a₃ and 326b₁-326b₃ may be replaced with grooves or the like (not shown) formed in the outer surfaces of fingers 324a, 324b. The grooves may be configured and dimensioned to selectively receive a C-clamp or the like.

Figure 14:
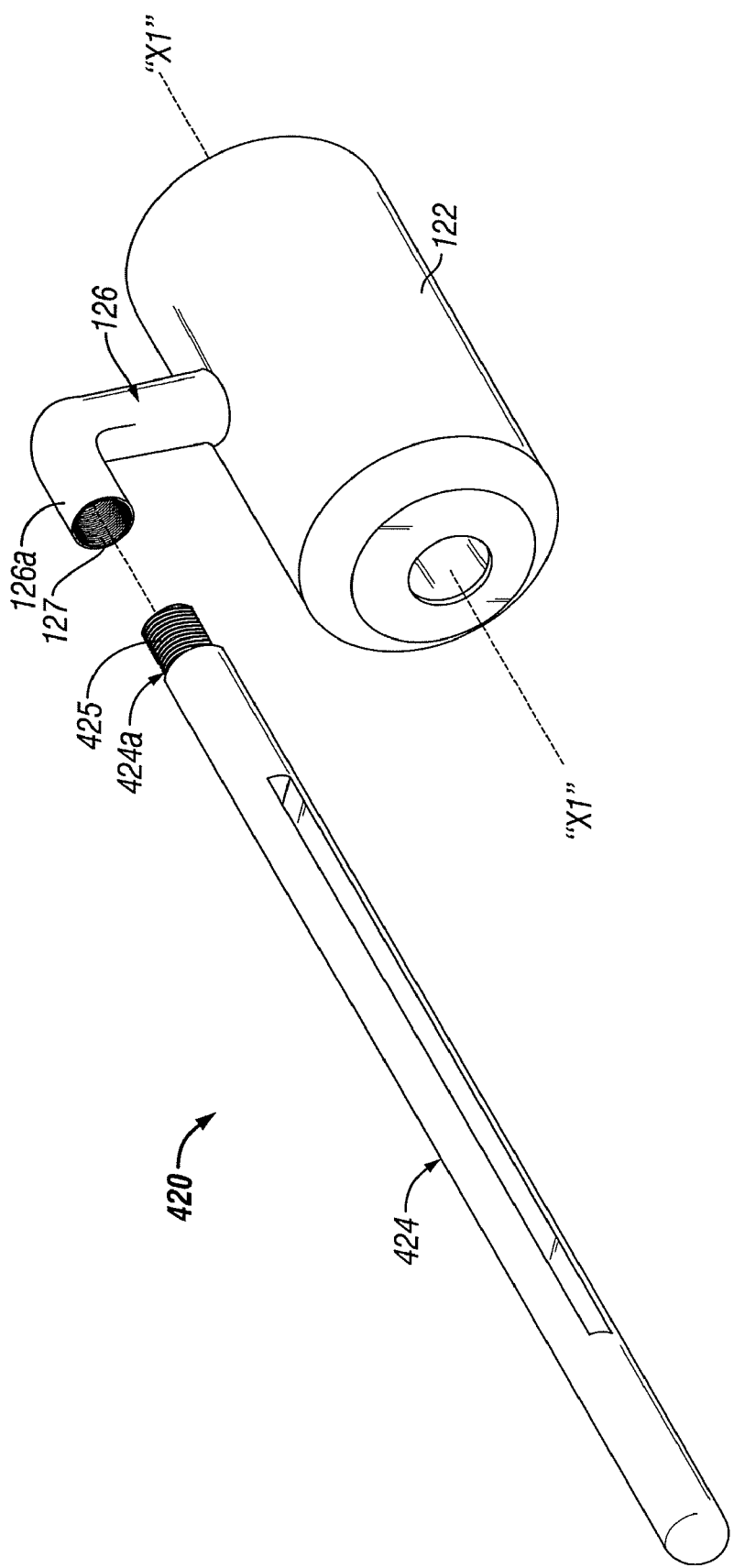
FIG. 14 is a perspective view, with parts separated, of a tensioning member according to yet another embodiment of the present disclosure.

Turning now to FIG. 14, an alternate embodiment of a tensioning member for use with rotary drive device 110 is generally designated as 420. Tensioning member 420 is substantially similar to tensioning member 120 and will only be discussed in detail to the extent necessary to identify differences in construction and operation.

As seen in FIG. 14, tensioning member 420 includes a tensioning arm 224 operatively connectable to leg 126. Desirably, leg 126 includes an elbow such that a distal end portion 126a thereof is oriented in a direction substantially parallel to the longitudinal "X1" axis of cuff 122. Desirably, distal end portion 126a of leg 126 defines an opening 127 therein for receiving a proximal end 424a of tensioning arm 424 therein.

Desirably, tensioning arm 424 includes a connecting member 425 extending axially from proximal end 424a thereof. Preferably, connecting member 425 includes a thread configured and dimensioned to engage a complementary thread formed within opening 127 of leg 126. It is envisioned that connecting member 425 may also include and is not limited to a bayonet-type connection for engaging a complementary member provided within opening 127, or proximal end 424a of tensioning arm 424 may be configured and dimensioned to friction fit within opening 127 of leg 126.

In this manner, tensioning arms 424 of various dimensions and/or materials may be selectively connected to leg 126 of cuff 122 and ultimately to rotary drive device 110. For example, a tensioning arm 424, specific to a particular bandage to be wrapped (e.g., a polo-wrap, a standing wrap, a tail wrap, etc.) may be attached to cuff 122 as needed.

Figure 15:
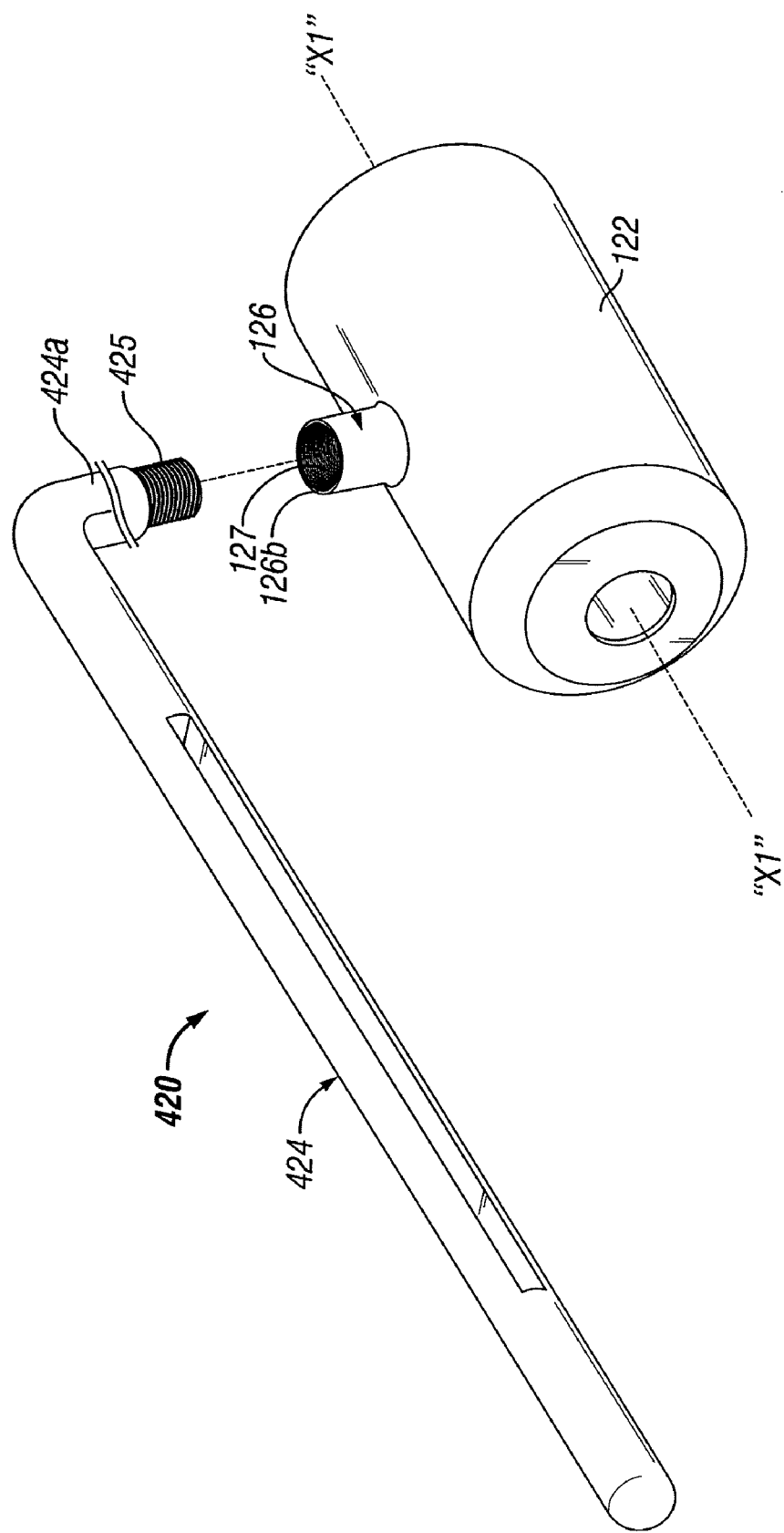
FIG. 15 is a perspective view, with parts separated, of a tensioning member according to a further embodiment of the present disclosure.

In an alternate embodiment, as seen in FIG. 15, a distal end portion 126b of leg 126 is oriented in a direction which is substantially orthogonal to the longitudinal "X1" axis of cuff 122. Desirably, distal end portion 126b of leg 126 defines an opening 127 therein for receiving a proximal end 424a of tensioning arm 424 therein.

Desirably, proximal end 424a of tensioning arm 424 is oriented orthogonally to a longitudinal axis of tensioning arm 424. Tensioning arm 424 includes a connecting member 425 extending axially from proximal end 424a. Preferably, connecting member 425 includes a thread configured and dimensioned to engage a complementary thread formed within opening 127 of leg 126. It is envisioned that connecting member 425 may also include and is not limited to a bayonet-type connection for engaging a complementary member provided within opening 127, or proximal end 424a of tensioning arm 424 may be configured and dimensioned to friction fit within opening 127 of leg 126. It is further envisioned that proximal end 424a of various tensioning arms 424 may have varying lengths. In this manner, a particular tensioning arm 424 having a particular length proximal end 424a is selected depending on the type and/or length of bandage to be wound onto winding peg 130. For example, for relatively longer bandages, tensioning arms 424 having relatively longer proximal ends 424a may be attached to leg 126 of cuff 122. In this manner, the distance between tensioning arm 424 and winding peg 130 is increased in order to accommodate a longer bandage when wound thereon.

Figure 16:
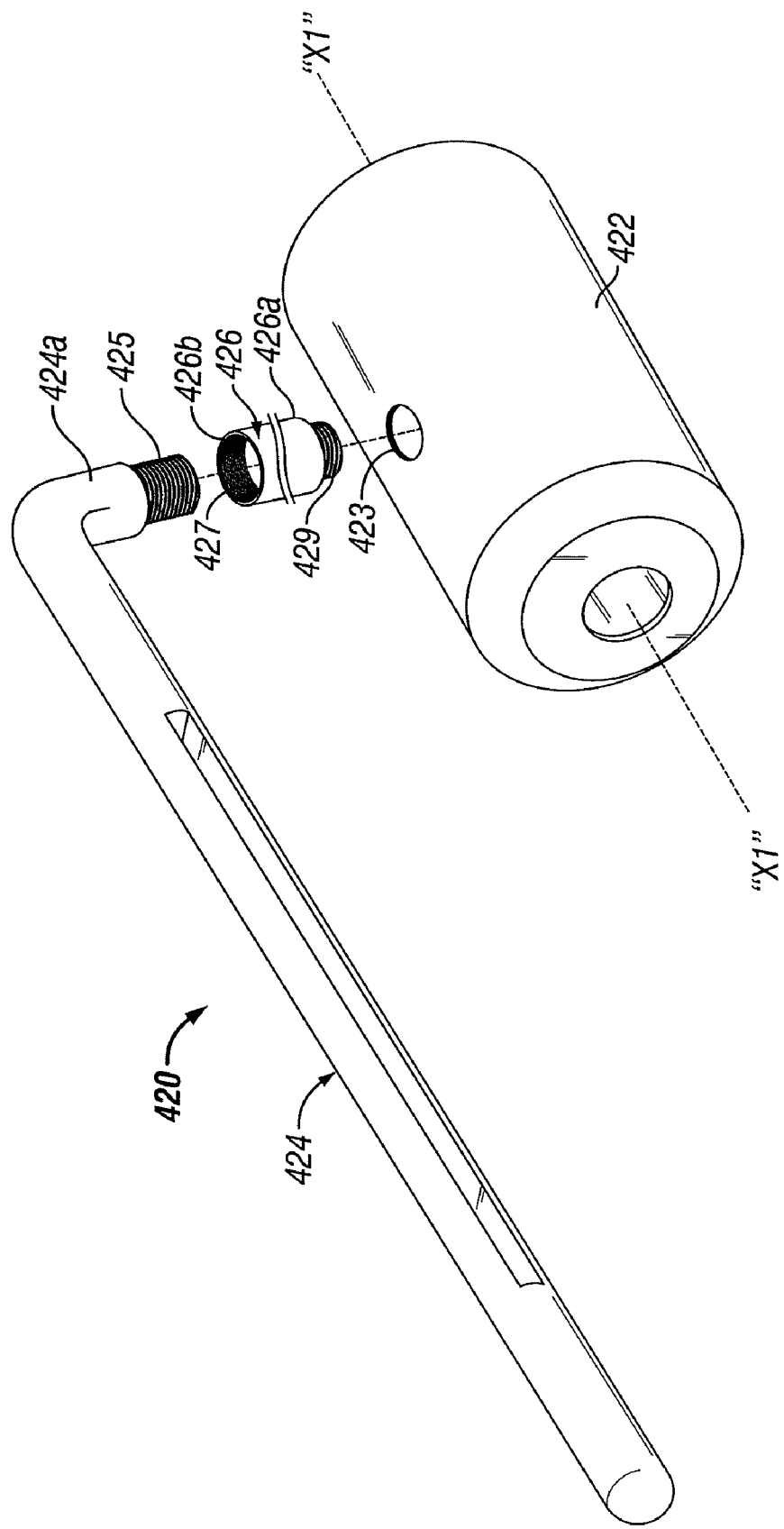
FIG. 16 is a perspective view, with parts separated, of a tensioning member according to still another embodiment of the present disclosure.

As seen in FIG. 16, tensioning member 420 may be entirely modular, including a cuff 422, a leg 426 selectively connectable to cuff 422 and/or housing 112 of rotary drive device 110, and a tensioning arm 424 selectively connectable to leg 426. Desirably, a plurality of legs 426 may be provided (not shown), each having a different length. In this manner, depending of the length of bandage "B" to be wound onto winding peg 130 (i.e., the prospective diameter of the wound bandage "B"), the leg 426 to be used in tensioning member 420 is selected based on its length. Accordingly, for relatively longer bandages "B", a relatively longer leg 426 may be selected and for relatively shorter bandages "B", a relatively shorter leg 426 may be selected. In this manner, tensioning member 420 may be configured as needed to accommodate the winding of bandages "B" of any length.

In particular, as seen in FIG. 16, cuff 422 includes a threaded opening 423 formed in the side thereof for selectively receiving a threaded connecting member 429 extending from a proximal end 426a of leg 426. Leg 426 includes a threaded opening 427 formed in a distal end 426b thereof for selectively receiving a threaded connecting member 425 extending from proximal end 424a of tensioning arm 424. A plurality of legs 426, each having a different length may be selectively connected to cuff 422. Accordingly, in use, depending of the length of bandage "B" to be wound onto winding peg 130 a leg 426 having a length sufficient to space tensioning arm 424 from winding peg 130 in order to accommodate the diameter of a wound bandage therebetween is connected to cuff 422.

In accordance with the present disclosure, it is envisioned that kit 200 may be configured and adapted to retain or house tensioning member 420, including cuff 422, tensioning arm 424 and a series of legs 426 of varying length.

Figure 17:
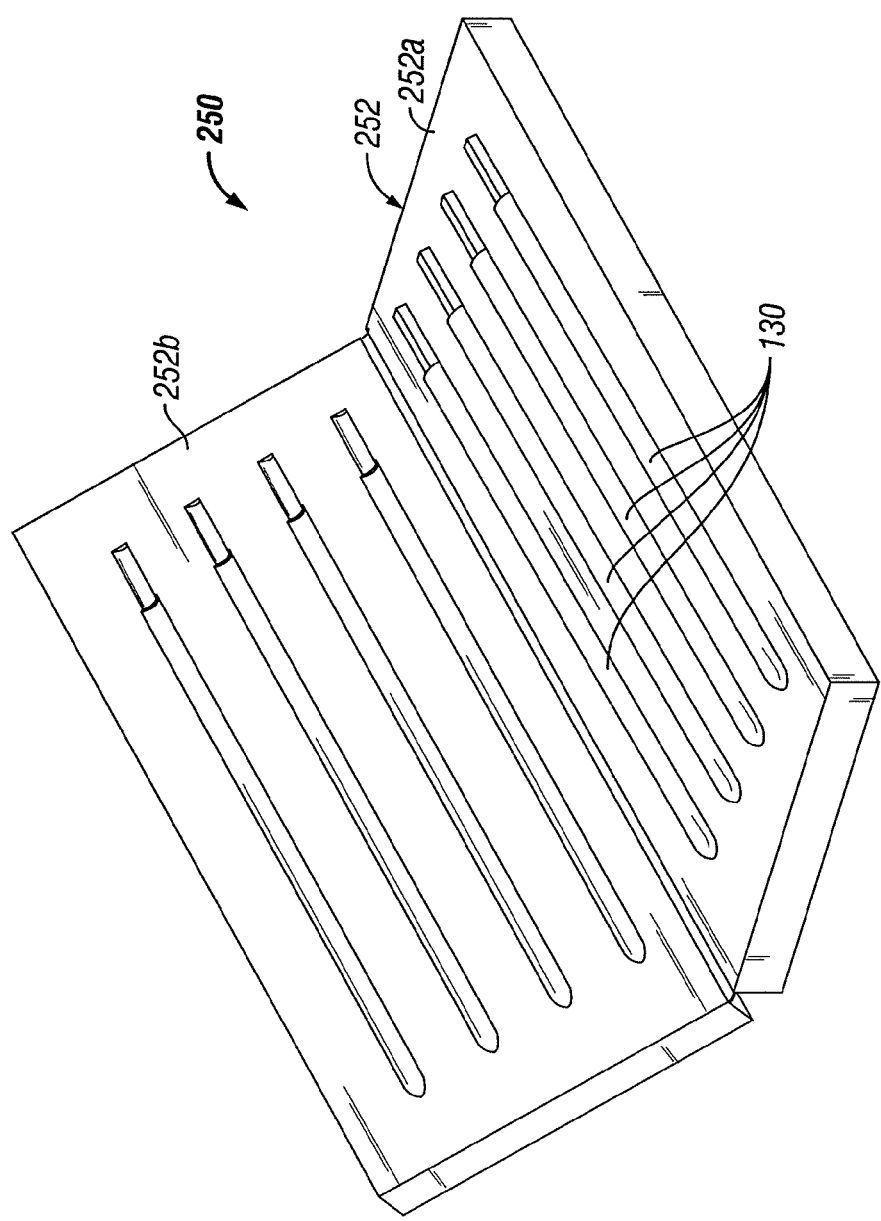
FIG. 17 is a perspective view of one illustrative embodiment of a kit including a plurality of winding pegs of FIG. 6.

Turning now to FIG. 17, a kit 250, according to an embodiment of the present disclosure, including a plurality of winding pegs 130 is shown. Kit 250 includes a case 252 having a bottom case portion 252a, and a lid or top case portion 252b hingedly connected (e.g., via a living hinge) to bottom case portion 252a.

Case 252 of kit 250 is configured and adapted to contain a plurality of winding pegs 130. Case 252 may be fabricated from molded plastic and the like configured and dimensioned to accommodate the plurality of winding pegs 130 in a snap-fit engagement.

Figure 18:
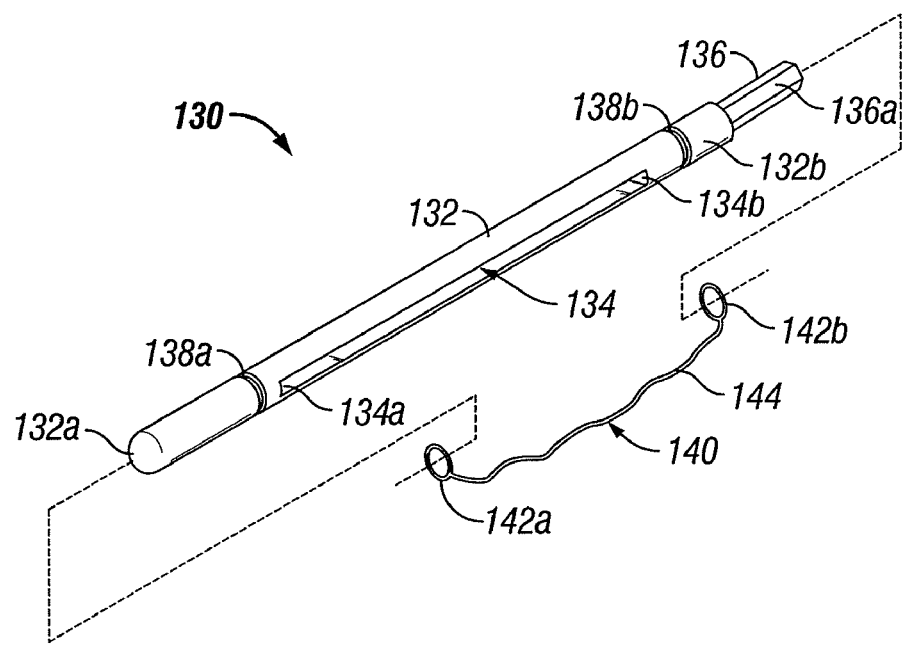
FIG. 18 is a perspective view of a winding peg according to another embodiment of the present disclosure, and a tie-down element for use therewith.
Figure 19:
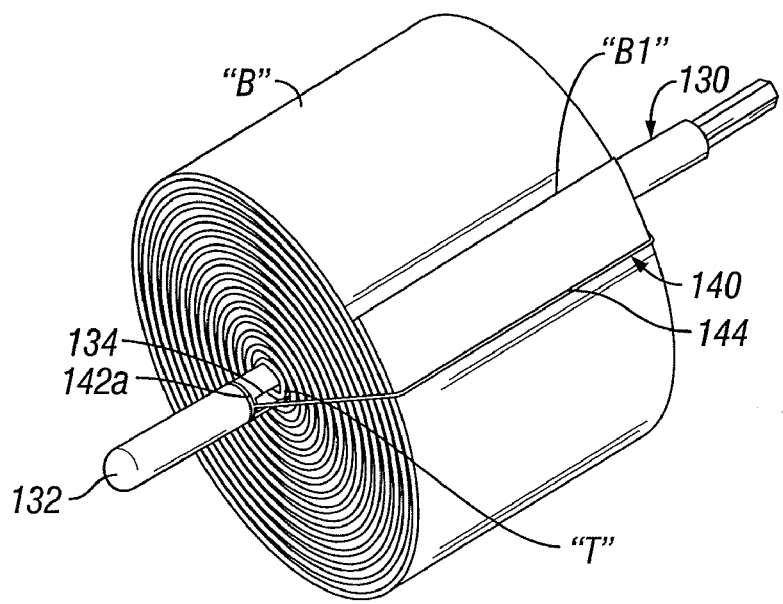
FIG. 19 is a perspective view of the winding peg of FIG. 18 including a bandage wound thereon and the tie-down element extending thereacross.

Turning now to FIGS. 18 and 19, an alternate embodiment of winding peg 130, in accordance with the present disclosure, is shown and described. As seen in FIG. 18, winding peg 130 further includes an annular distal groove 138a formed in body portion 132 provided at a location distal of slot 134. Desirably, winding peg 130 may also include an annular proximal groove 138b provided at a location proximal of slot 134.

As seen in FIG. 18, a tie-down element 140 for extending between a distal end of winding peg 130 and a proximal end of winding peg 130, desirably across a rolled-up bandage "B", is provided. Tie-down element 140 include a first ring 142a, a second ring 142b, and a band or strap 144 extending between first ring 142a and second ring 142b. Rings 142a, 142b are configured and dimensioned to slide over a respective one of the distal end of winding peg 130 and stem 136 of winding peg 130. Additionally, ring 142a is configured and dimensioned to operatively engage (e.g., be received in, be seated in, etc.) annular distal groove 138a of winding peg 130 and ring 142 is configured and dimensioned to operatively engage annular proximal groove 138b or stem 136 of winding peg 130. Rings 142a, 142b may be fabricated from a rigid material, such as, for example, plastic, metal and the like. It is also envisioned and contemplated that rings 142a, 142b may be loops or eye-lets formed at either end of strap 144 from the same material as strap 144. Strap 144 is desirably made from an elastic material or the like. In this manner, band 144 may stretch and/or elongate as needed in order to extend across rolled-up bandages of varying diameters.

As seen in FIG. 19, with bandage "B" wound onto winding peg 130, tie-down element 140 is used to keep bandage "B" from un-winding. In particular, first ring 142a may be slipped over the distal end of winding peg 130 and slid down body portion 132 until first ring 142a engages annular distal groove 138a, band 144 stretched across bandage "B", and second ring 142b slipped over stem 136 of winding peg 130 and slid up body portion 132 until second ring 142b engages annular proximal groove 138b. It is further envisioned that second ring 142b may be positioned on stem 136. Desirably, band 144 is positioned in close proximity to a free end "B1" of bandage "B".

While tie-down element 140 has been shown and described as being used with a winding peg 130 having an annular distal groove 138a and possibly an annular proximal groove 138b, it is envisioned and within the scope of the present disclosure for tie-down element 140 to be used with a winding peg 130 having no annular grooves formed therein in substantially the same manner as with winding peg 130 having annular grooves 138a, 138b.

Figure 20:
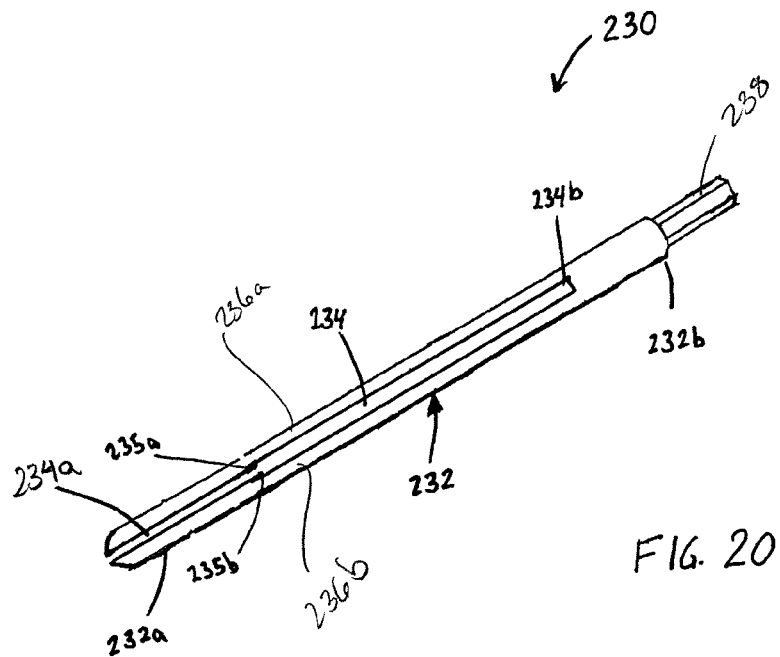
FIG. 20 is a perspective view of a winding peg according to another embodiment of the present disclosure.
Figure 21:
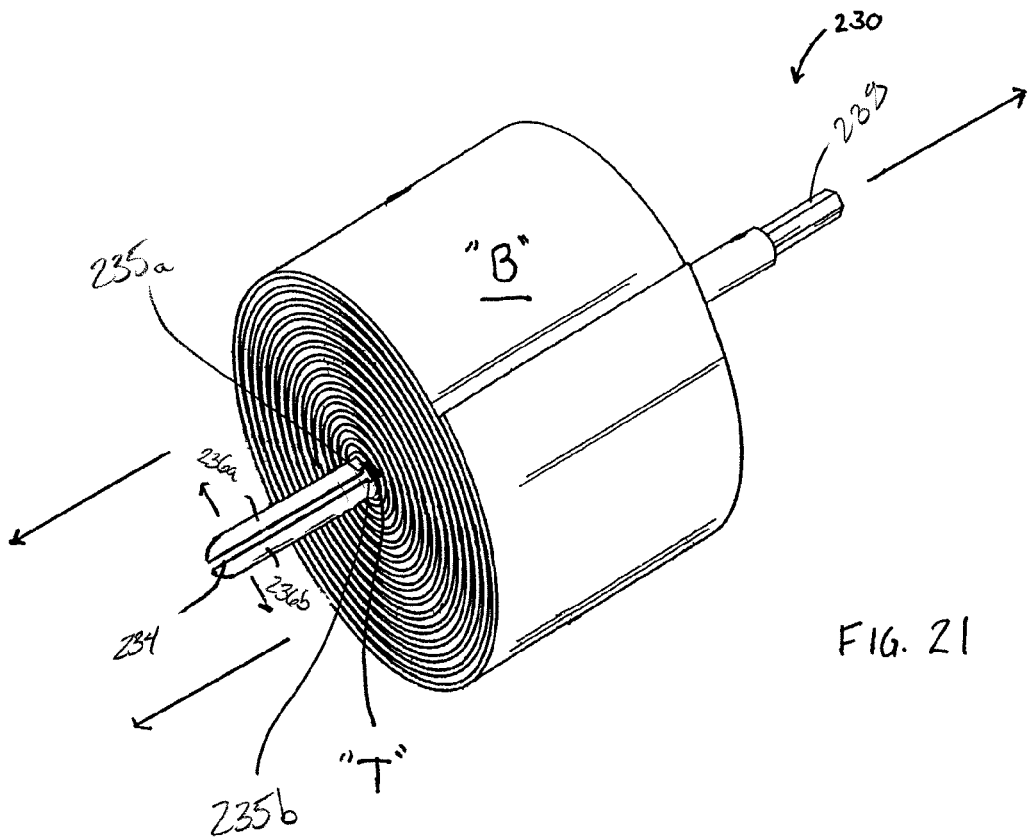
FIG. 21 is a perspective view of the winding peg of FIG. 20 including a bandage wound thereon.

Turning now to FIGS. 20 and 21, an alternate embodiment of a winding peg for use with rotary drive device 110 is generally designated as 230. Winding peg 230 includes an elongate body portion 232 having a distal end portion 232a and a proximal end portion 232b. Winding peg 230 includes a slot 234 formed therein. Slot 234 is bounded, or defined, by a closed proximal end 234b and an open distal end 234a. In this manner, bandage "B" may slide into position within slot 234 of winding peg 230 through open distal end 234a. Once wound about winding peg 230, bandage "B" may be removed from about winding peg 230 through open distal end portion $^2$32a.

Distal end portion 232a of body portion 232 forms fingers or projections 235a, 235b which define a slot 234. Distal end 234a of slot 234 is narrower than proximal end 234b of slot 234, thereby forming shoulders 235a, 235b for retaining bandage "B" within slot 234. Shoulders 235a, 235b, defining open distal end portion 234a and slot 234, are dimensioned such that bandage "B" cannot pass through open distal end portion 232a without the deflection of fingers 236a, 236b away from one another. In this manner, bandage "B" may be received through distal end 234a of slot 234 and is more securely retained within slot 234 than bandage "B" would be if slot 234 had a uniform height.

FIGS. 236a, 236b are integrally formed with body portion 232. In alternate embodiment the fingers 236a, 236b may be of any length and constructed from plastic, metal or the like. Fingers 236a, 236b may define slot 234 of any dimension, preferably sized to receive a bandage "B" therethrough. By way of example only, slot 234 of winding peg 230 may have a height of about 0.125 inches, although other heights are envisioned, contemplated and within the scope of the present disclosure.

Winding peg 230 includes a connecting member or stem 238 extending axially from proximal end potion 232b of body portion 232. Stem 238 is configured and adapted to be inserted into and/or matingly received in chuck 114 of rotary drive device 110.

As seen in FIG. 21, with tab "T" of bandage "B" inserted into slot 234 of winding peg 230, winding peg 230 has been wound in order to roll-up bandage "B" thereon and to thereby form bandage "B" into a cylinder, drum or the like. In accordance with the present disclosure, since slot 234 includes an open distal end 234a, bandage "B" may slide out of distal end portion 232a of body portion 232. As discussed above, fingers 236a, 236b defining slot 234 must be deflected away from one another in order for bandage "B" to pass through. Bandage "B" may be removed from winding peg 232 regardless of whether winding peg 232 remains securely attached to rotary drive device 110.

Figure 22:
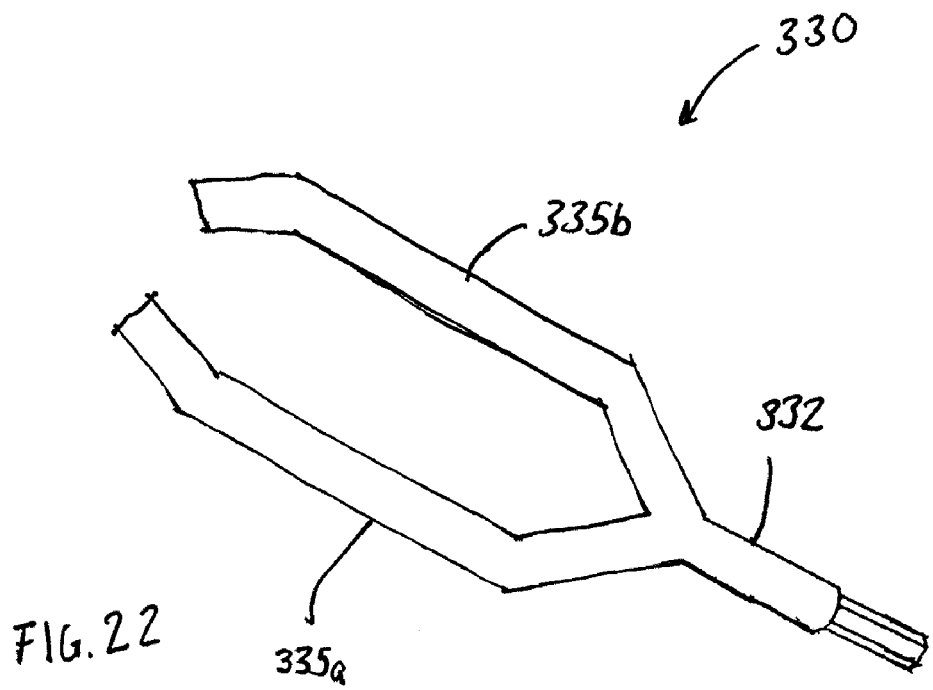
FIG. 22 is a perspective view of a winding peg according to yet another embodiment of the present disclosure.
Figure 23:
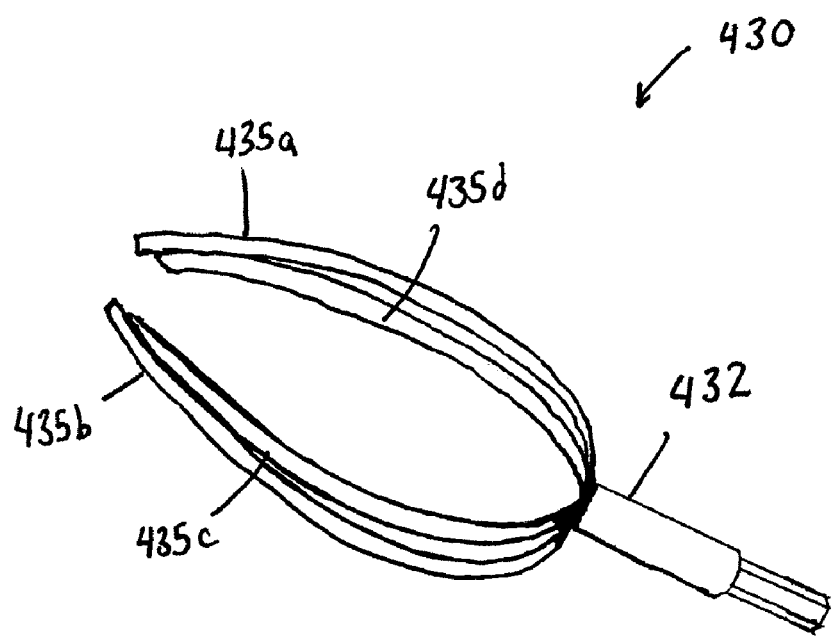
FIG. 23 is a perspective view of a winding peg according to another embodiment of the present disclosure.

Referring now to FIGS. 22 and 23, alternate embodiments of a winding peg for use with rotary drive device 110 are shown and are generally designated as 330, 430, respectively. Winding pegs 330, 430 are substantially similar to winding peg 230 and will only be discussed in detail to the extent necessary to identify differences in construction and operation.

As seen in FIG. 22, winding peg 330 includes a pair of spaced apart fingers 335a, 335b oriented for receiving a bandage therebetween. Fingers 335a, 335b may be securely fixedly to base portion 332 or may be integrally formed with base portion 332. Fingers 335a, 335b form a tweezers style configuration wherein a tab "T" of a bandage "B" (not explicitly shown) is inserted between spaced apart fingers 335a, 335b. As bandage "B" is wound about winding peg 330, fingers 335a, 335b are deflected towards one another in a tweezers-like motion. As with winding peg 230, bandage "B" may be removed from winding peg 330 once wound thereon by sliding bandage "B" off of the distal of end fingers 335a, 335b.

As seen in FIG. 23, winding peg 430 includes a plurality of fingers 435a-435d for receiving bandage "B". Fingers 435a-435d may be securely fixed to or integrally formed with base portion 432. Fingers 435a-435d form a generally tear drop shaped configuration wherein a tab "T" of a bandage "B" (not explicitly shown) may be inserted between open fingers 435a-435d. As bandage "B" is wound about winding peg 430, fingers 435a-d deflect towards one another, thereby flattening the tear drop shaped configuration and more securely retaining bandage "B" therebetween. Like winding peg 330, winding peg 430 also allows for the removal of wound bandage "B" from arms 435a-435d by sliding bandage "B" off of the distal end of fingers 435a-435b.

Figure 24:
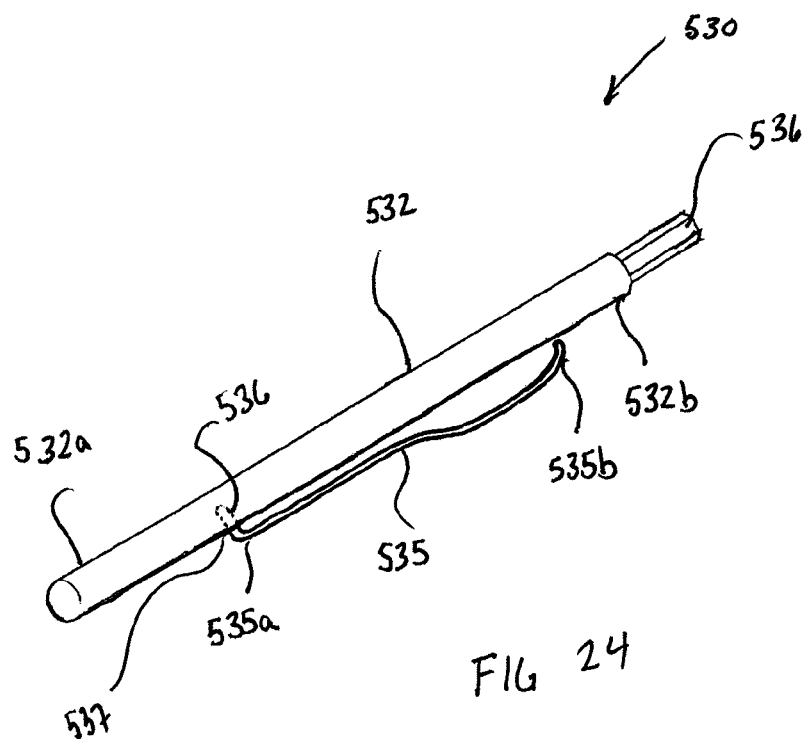
FIG. 24 is a perspective view of a winding peg according to still another embodiment of the present disclosure.
Figure 25:
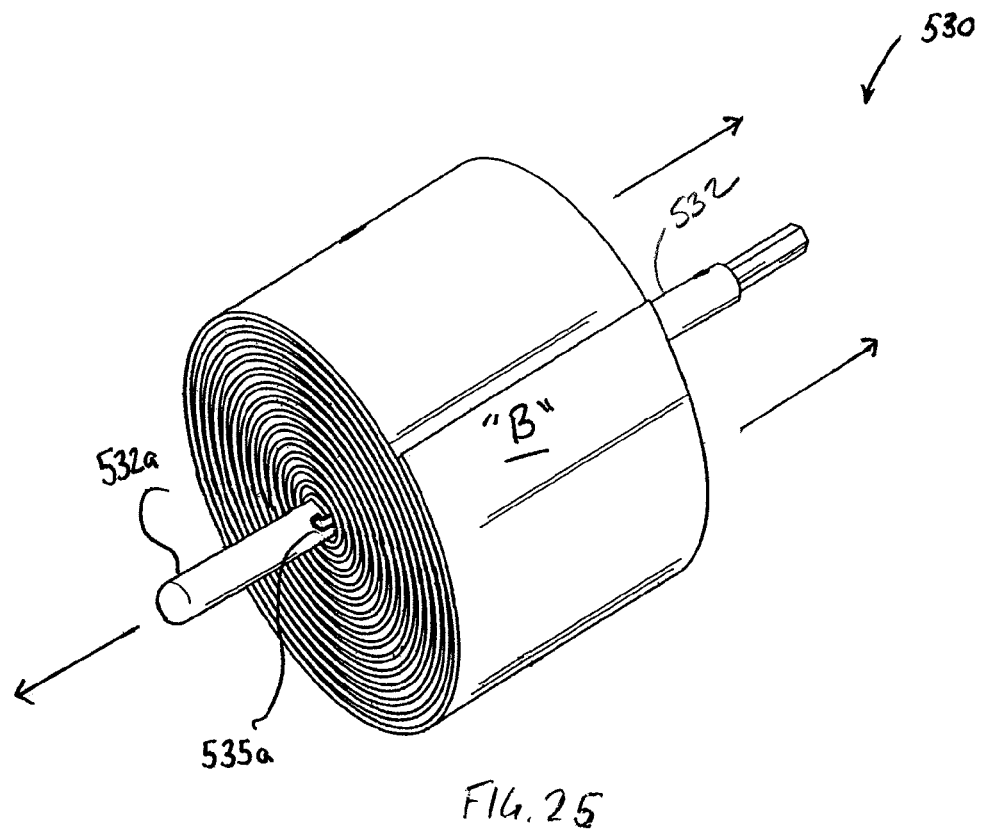
FIG. 25 is a perspective view of the winding peg of FIG. 24 including a bandage wound thereon.

Turning now to FIGS. 24 and 25, an alternate embodiment of a winding peg for use with a rotary drive device 110 is generally designated as 530. As with the previously disclosed winding pegs, winding peg 530 includes an elongate body portion 532 having a distal end portion 532a and a proximal end portion 532b. Winding peg 530 also includes a connecting member or stem 536 extending axially from proximal end potion 532b of body portion 532. Stem 536 is configured and adapted to be inserted into and/or matingly received in chuck 114 of rotary drive device 110 (see FIGS. 1-3).

Winding peg 530 further includes a clip 535 for selectively receiving a tab "T" of bandage "B" (not explicitly shown). Clip 535 includes a distal end portion 535a and a proximal end portion 535b. Distal end portion 535a of clip 535 is fixedly attached to distal end portion 532a of body portion 532 of winding peg 530. Distal end portion 535a of clip 535 may have a tab or finger 536 designed and oriented to be received within a recess 537 formed in winding peg 530. Tab 536 of distal end portion 535a may be frictionally attached within recess 537 of winding peg 530. Tab 536 may further be adhered within recess 537 of winding peg 530 with glue, epoxy or the like. In an alternate embodiment, clip 535 may be fixedly attached to body portion 532 of winding peg 530 with tape, glue or the like.

Clip 535 of winding peg 530 extends proximally along body portion 532. Proximal end portion 535a of clip 535 is spaced a distance from body portion 532 so as to form an opening for receiving bandage "B" between clip 535 and body portion 532 of winding peg 530. In this manner, once bandage "B" is wound about winding peg 530, the bandage cannot be removed from winding peg 530 without disconnecting winding peg 530 from rotary drive device 110. This configuration of winding peg 530 and clip 535 ensures that bandage "B" will remain on winding peg 530 during use. Only once winding peg 530 has been disconnected from rotary device 110 can the bandage be removed from winding peg 530 by sliding bandage "B" off of proximal end portion 532b thereof.

Clip 535 may be constructed of any material, including plastic and metal. Clip 535 must be flexible enough to allow tab "T" of bandage "B" to be slipped from under clip 535. By way of example only, clip 535a of winding peg 530 may have a length of about 0.375 inches, although other heights are envisioned, contemplated and within the scope of the present disclosure.

Figure 26:
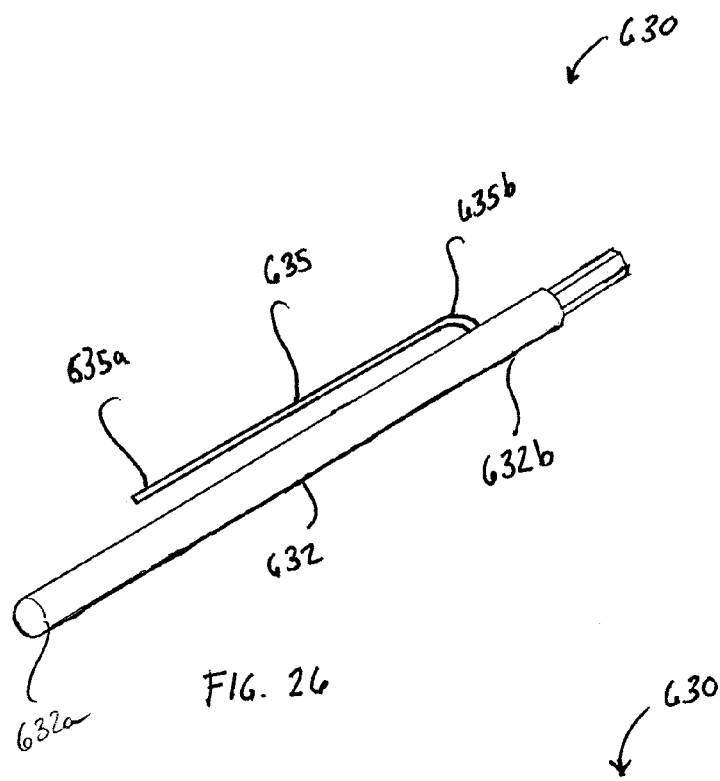
FIG. 26 is a perspective view of a winding peg according to a further embodiment of the present disclosure.
Figure 27:
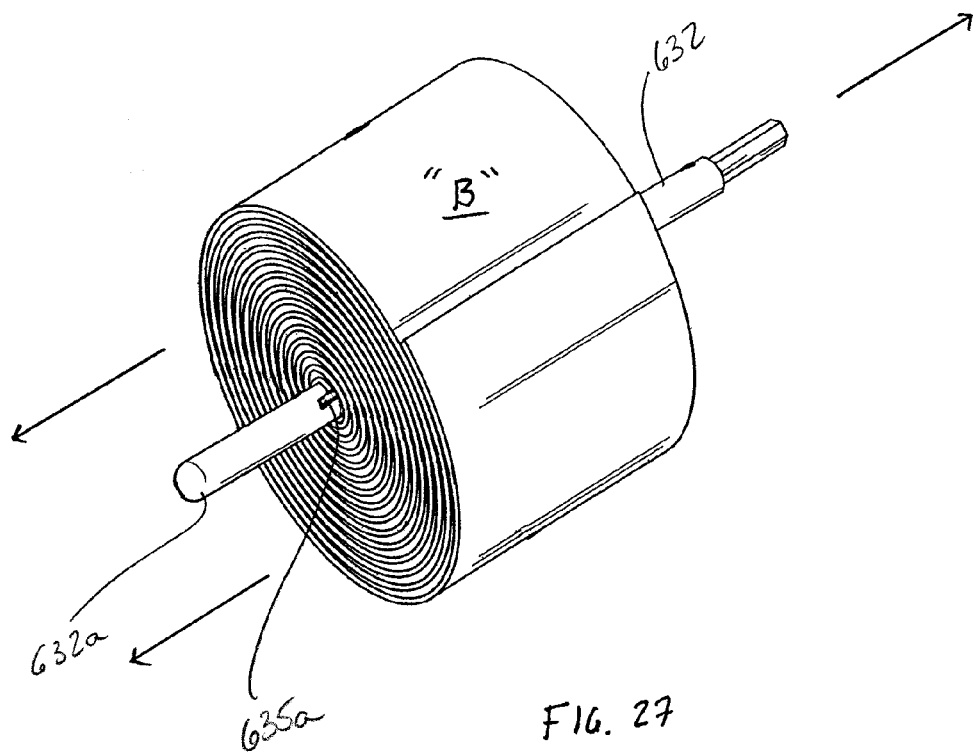
FIG. 27 is a perspective view of the winding peg of FIG. 26 including a bandage wound thereon.

Turning now to FIGS. 26 and 27, an alternate embodiment of a winding peg for use with rotary drive device 110 is generally designated as 630. Winding peg 630 is substantially similar to winding peg 530 and will only be discussed in detail to the extent necessary to identify differences in construction and operation. Clip 635 includes a distal end portion 635a and a proximal end portion 635b. Proximal end portion 635b of clip 635 is fixedly attached to proximal end portion 632b of winding peg 630. Clip 635 of winding peg 630 extends distally along body portion 632. Unlike with winding peg 530 and clip 535, the configuration of clip 635 allows bandage "B" to be removed from distal end portion 632a of base portion 632 while winding peg 630 remains secured to chuck 114 of rotary drive device 110.

Figure 28:
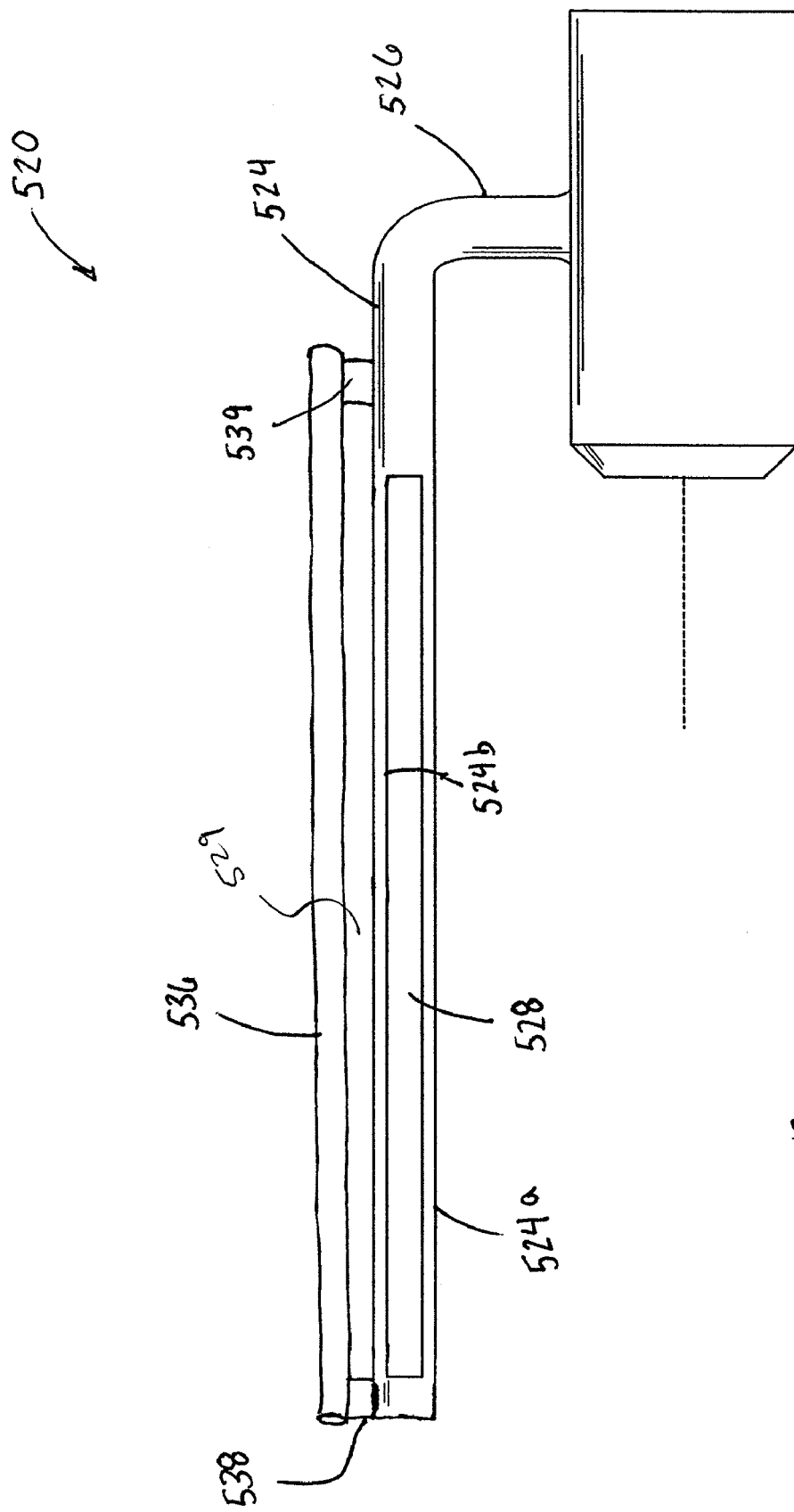
FIG. 28 is an elevational view of a tensioning arm according to another embodiment of the present disclosure.

Referring now to FIG. 28, an alternate embodiment of a tensioning member for use with rotary drive device 110 is generally designated as 520. Tensioning member 520 is substantially similar to tensioning member 120 and will only be discussed in detail to the extent necessary to identify differences in construction and operation.

As seen in FIG. 28, tensioning member 520 includes a tensioning arm 524 operatively connected to a leg 526 extending from base 522. Tensioning arm 524 includes a pair of parallel spaced apart fingers 524a, 524b defining a slot 528 therebetween. Tensioning member 520 further includes a drag bar 536 fixedly attached to proximal and distal ends of tensioning arm 524. Drag bar 536 may be substantially cylindrical, but may define any form in which a bandage "B" may freely pass thereover. Drag bar 536 extends substantially the entire length of slot 528. Drag bar 536 is attached to the exterior side of tensioning arm 524 by mounts 538, 539 so as to define a second slot 529 between finger 524b and drag bar 536. Mounts 538, 539 may be integrally formed with, or securely affixed to, tensioning arm 524. Mounts 538, 539 may also be integrally formed with, or securely affixed to, drag bar 536. In one embodiment, drag bar 536 is approximately ¼" of an inch in diameter and the gap distance between drag bar 536 and tensioning arm 524 measures 3/32" (inch).

In use, bandage "B" would be inserted, tab "T" first, through second slot 539, and fed through slot 528 in tensioning arm 524, and then inserted into the slot of a winding peg, as disclosed herein above.

Figure 29:
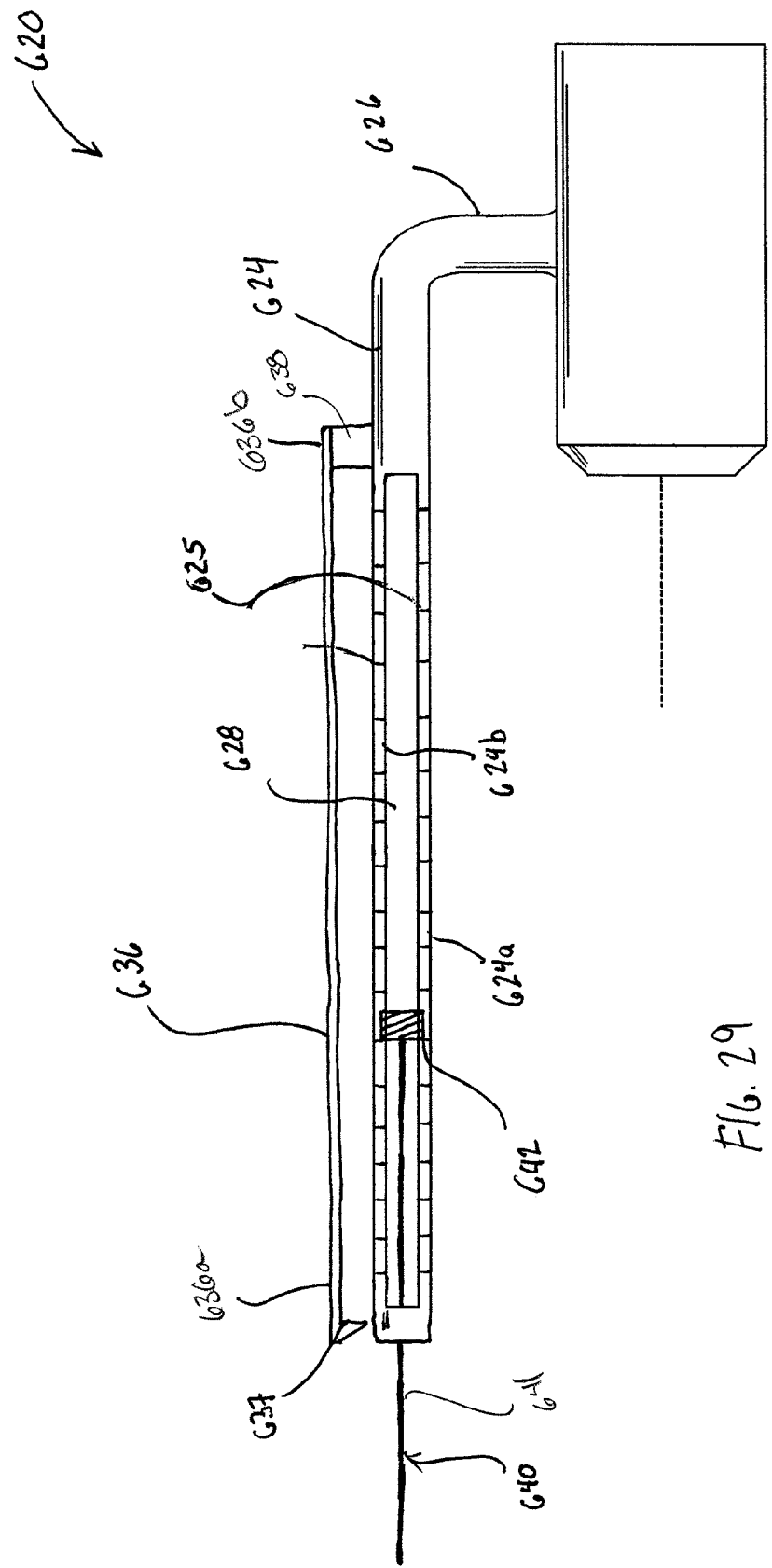
FIG. 29 is an elevational view of a tensioning arm according to yet another embodiment of the present disclosure.

Referring now to FIG. 29, an alternate embodiment of a tensioning member for use with rotary drive device 110 is generally designated as 620. Tensioning member 620 is substantially similar to tensioning member 520 and will only be discussed in detail to the extent necessary to identify differences in construction and operation.

As seen in FIG. 29, tensioning member 620 includes a tensioning arm 624 operatively connected to leg 626 extending from base 622. Tensioning arm 624 includes a pair of parallel spaced apart fingers 624a, 624b defining a slot 628 therebetween. At least one finger member 624a, 624b includes ruled markings 625 along the length of slot 628.

Tensioning member 620 further includes a drag bar 636 fixedly attached to tensioning arm 624. Like drag bar 536, drag bar 636 may be substantially cylindrical in shape, but may define any form in which a bandage "B" may freely pass thereover. Drag bar 636 extends substantially the entire length of slot 628. Drag bar 636 defines a proximal end 636b and a distal end 636a. Proximal end 636b of drag bar 636 is attached to the exterior side of a proximal end of tensioning arm 624 by a mount 638. Mount 638 may be integrally formed with, or securely affixed to, tensioning arm 624 by any known means. Mount 638 may also be integrally formed with, or securely affixed to, drag bar 636. Distal end 636a of drag bar 636 may include a tab 637 extending toward tensioning arm 624 for preventing bandage "B" from slipping from between drag bar 636 and tensioning arm 624. In an alternate embodiment, distal end 636a of drag bar 636 rather than proximal end 636b may be securely affixed to the distal end of tensioning arm 624.

Additionally, tensioning arm 624 includes a mechanism 640 for selectively adjusting the height or length of slot 628. Adjustment sleeve 640 includes a rod 641 passing through an opening in the distal end of tensioning arm 624. Rod 640 may be smooth, threaded, notched, or the like. The opening in the distal end of tensioning arm 624 is configured to receive rod 641 therethrough. Adjustment sleeve 640 further includes an adjusting block 642 operatively connected with rod 640. Adjusting block 642 is positioned within and/or about slot 628 and is slidably positionable along slot 628. In operation, rotation of rod 641 causes block 642 to slide along slot 628, thereby adjusting the height and/or length thereof. Rotation of rod 641 in a direction such that rod 641 is extracted from the distal end of tensioning arm 624 results in the height or length of slot 628 to increase. Rotation of rod 641 in an opposite direction will result in the height or length of slot 628 to decrease.

Alternate embodiments of mechanism 640 for selectively adjusting the height of slot 628 have been contemplated by this disclosure. For example, rod 646 may be frictionally slidably received within the distal end of tensioning arm 624. In a further embodiment, mechanism 640 includes a fastener (not shown) to selectively prevent the movement of rod 641 within tensioning arm 624.

In yet another embodiment of mechanism 640, a rod 641 is not employed to adjust the height or length of slot 628. Instead, adjusting block 642 is frictional received within slot 628. Adjusting block 642 may further be held in place through the use of mechanical fasteners. In still yet another embodiment, adjusting block 642 may form a selectively positionable ring configured to slide over and/or about tensioning arm 624. Additionally, adjusting block 642 may be threadingly disposed within or about slot 628, such that as adjusting block 642 is rotated adjusting block 624 moves longitudinally along slot 628.

Referring now to FIGS. 30-36B, alternate embodiments of a tensioning member for use with rotary drive device 110 are generally designated as 720, 820, 920, 1020, respectively. Tensioning members 720, 820, 920, 1020 are substantially similar to tensioning member 120 and will only be discussed in detail to the extent necessary to identify differences in construction and operation.

Figure 30:
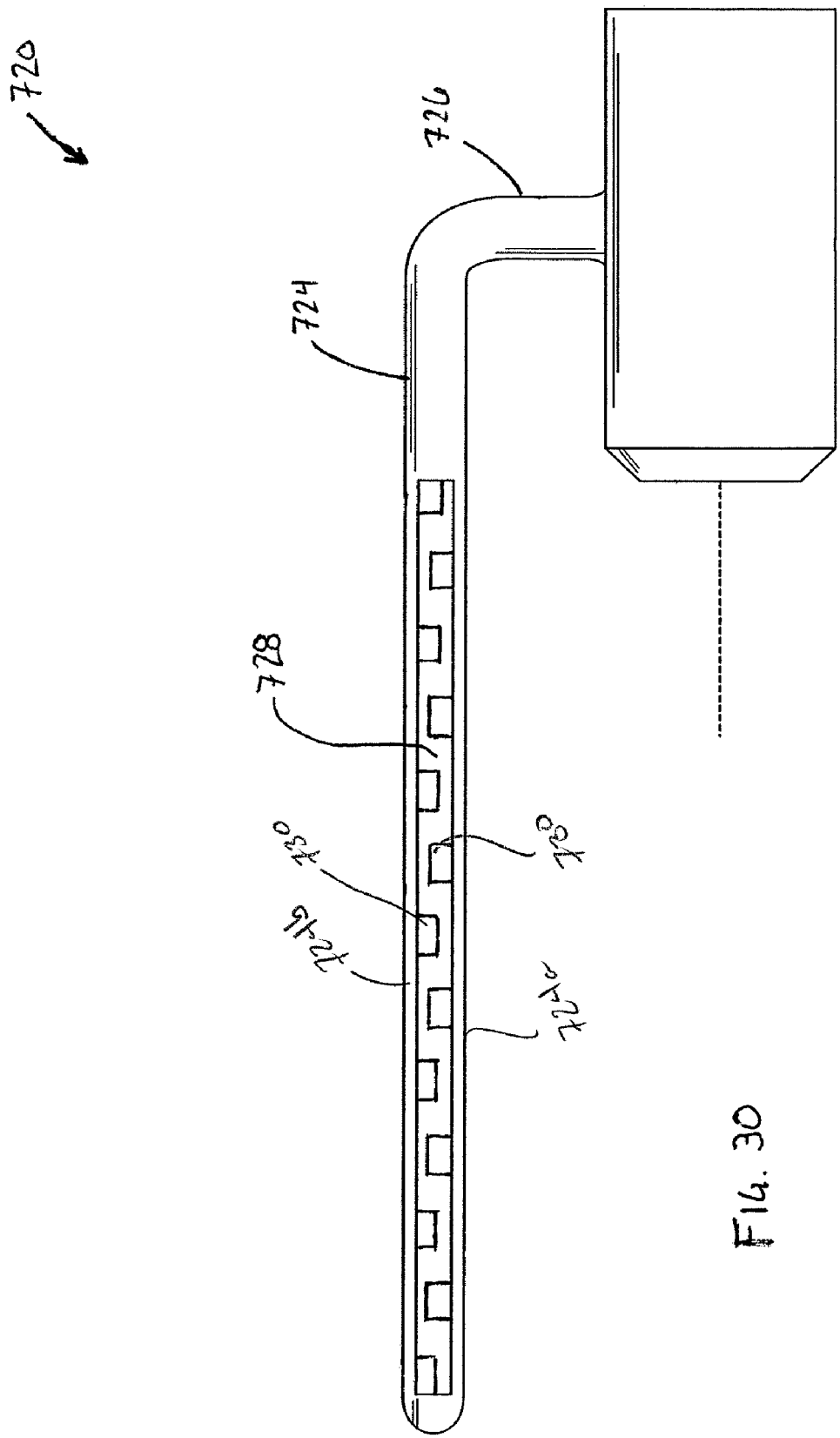
FIG. 30 is an elevational view of a tensioning arm according to still another embodiment of the present disclosure.

As seen in FIG. 30, tensioning member 720 includes a tensioning arm 724 operatively connected to leg 726 extending from base 722. Tensioning arm 724 includes a pair of parallel spaced apart fingers 724a, 724b defining a slot 728, therebetween. Each finger 724a, 724b is configured to include protrusions 730 extending into slot 728. Protrusions 730 of fingers 724a, 724b are positioned alternately along slot 728. Protrusions 730 may be integrally formed with fingers 724a, 724b. Protrusions 730 may be secured to the slot forming surfaces of fingers 724a, 724b by mechanical fasteners, adhesive or the like. Protrusions 730 may be rectangular, square, triangular, teardrop, oval, etc. in cross-sectional profile. Protrusions 730 may be solid or hollow. Protrusions 729 may further be configured to permit unidirectional movement of bandage "B" through slot 728. In this way, protrusions 729 maintain tension on, and prevent slippage of, bandage "B" as bandage "B" passes through slot 728 en route to being wound on any of the previously disclosed winding pegs.

Figure 31:
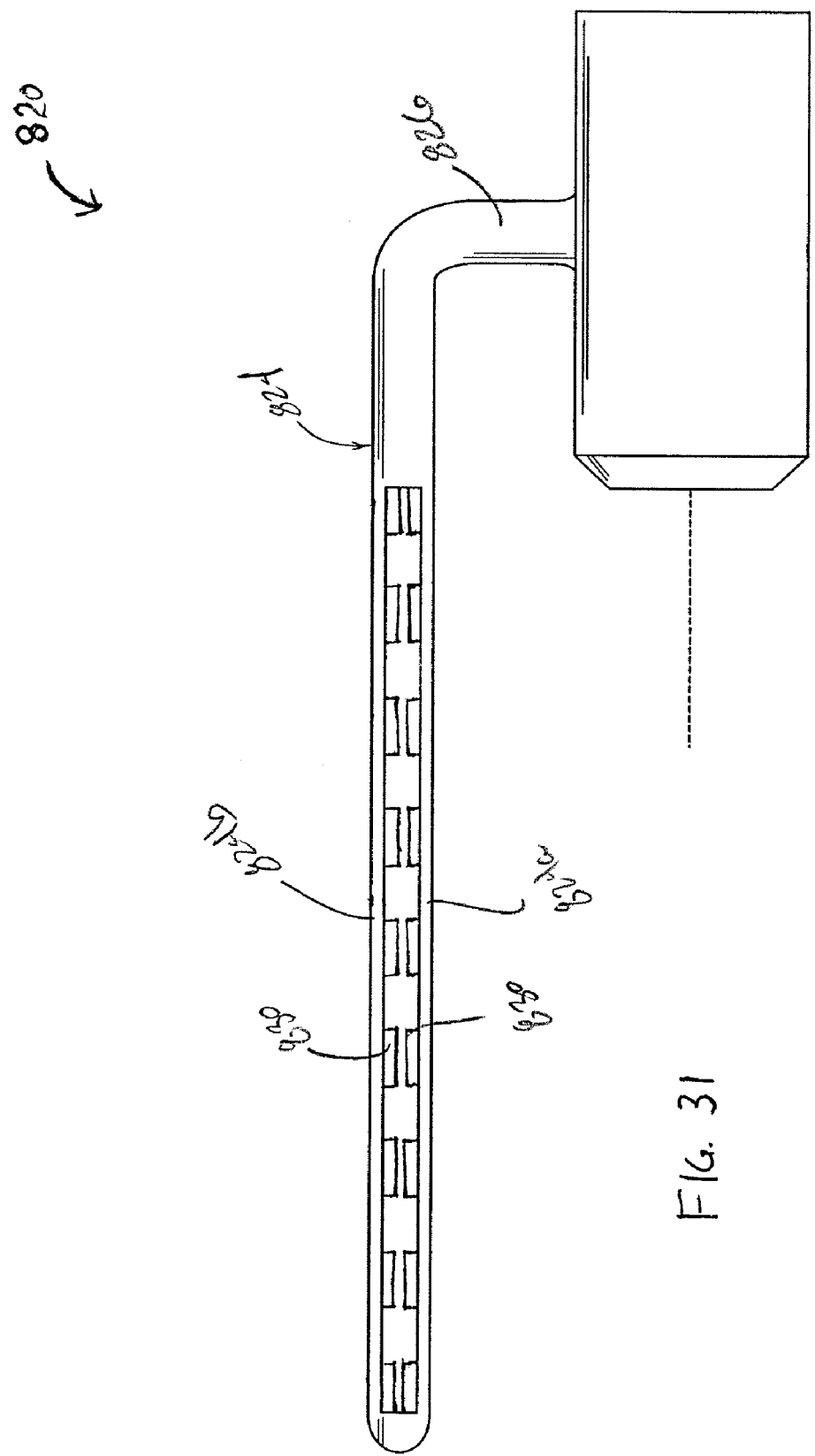
FIG. 31 is an elevational view of a tensioning arm according to a further embodiment of the present disclosure.

Referring now to FIG. 31, in an alternate embodiment, tensioning member 820 includes a tensioning arm 824 having a pair of parallel spaced apart fingers 824a, 824b. Each finger includes a plurality of protrusions 830 provided along the length thereof. Protrusions 830 of fingers 824a, 824b are in vertical alignment or registration with each other. As with tensioning member 720, protrusions 830 of tensioning member 820 may be configured to permit unidirectional movement of bandage "B" through slot 828 of tensioning arm 824.

Figure 32:
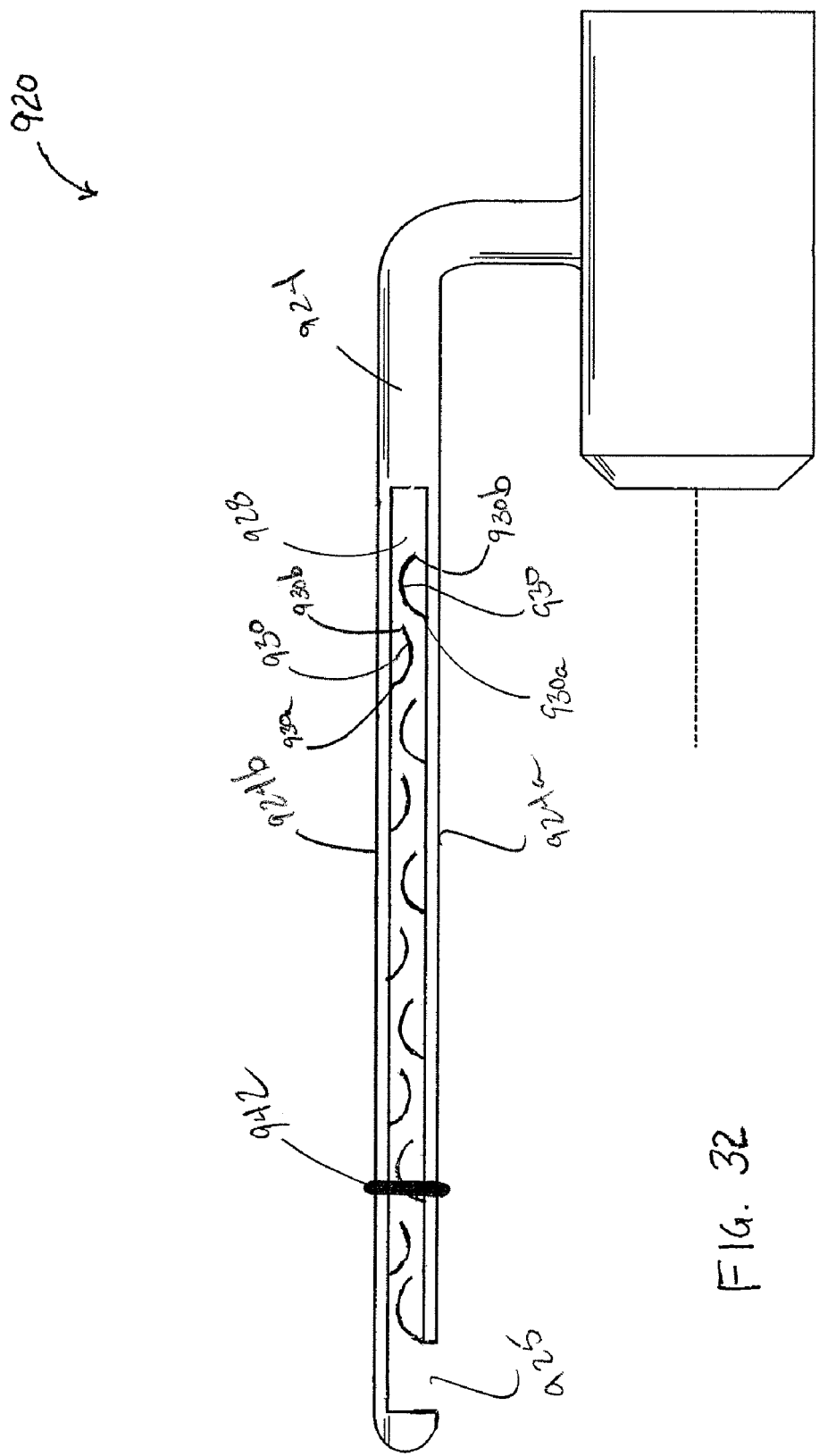
FIG. 32 is an elevational view of a tensioning arm according to still a further embodiment of the present disclosure.
Figure 33:
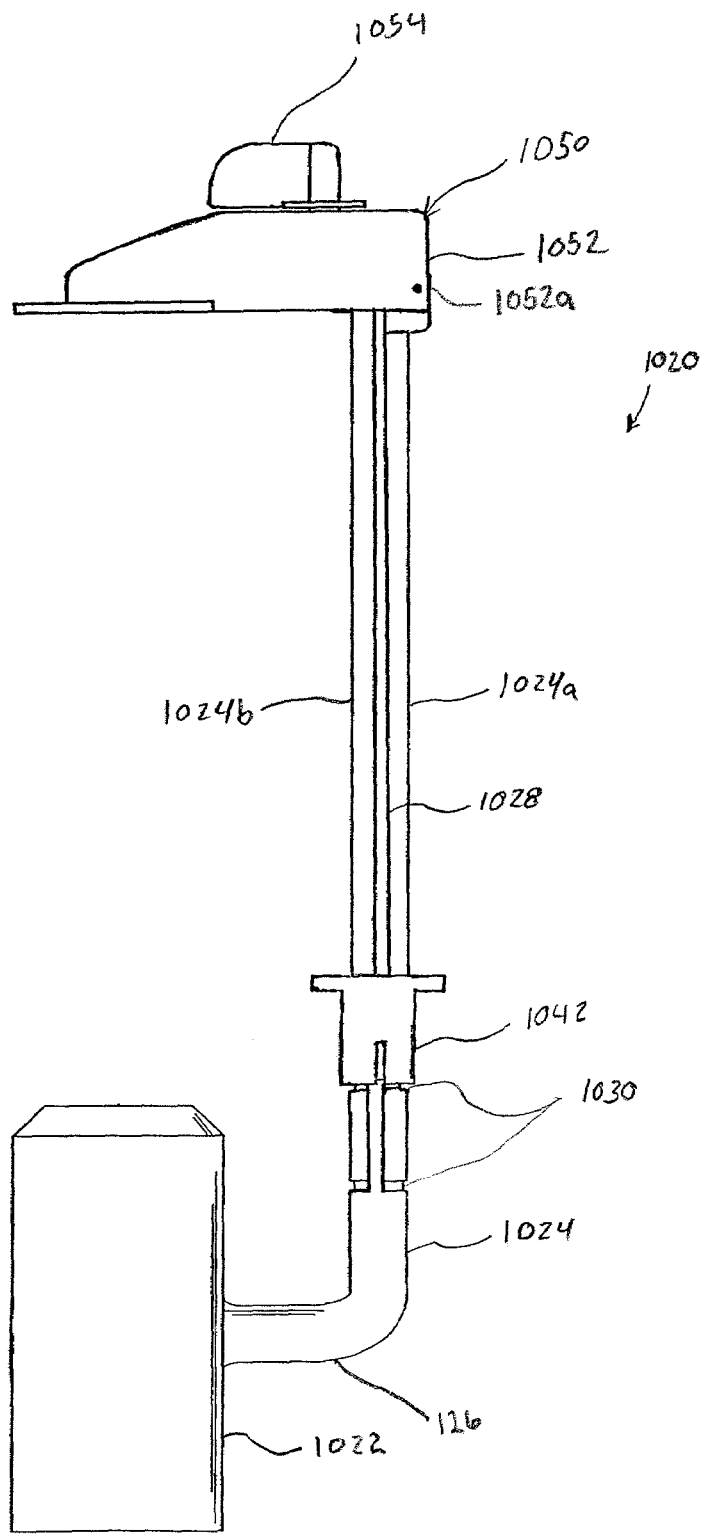
FIG. 33 is an elevational view of a tensioning arm according to still yet another embodiment of the present disclosure.
Figure 34:
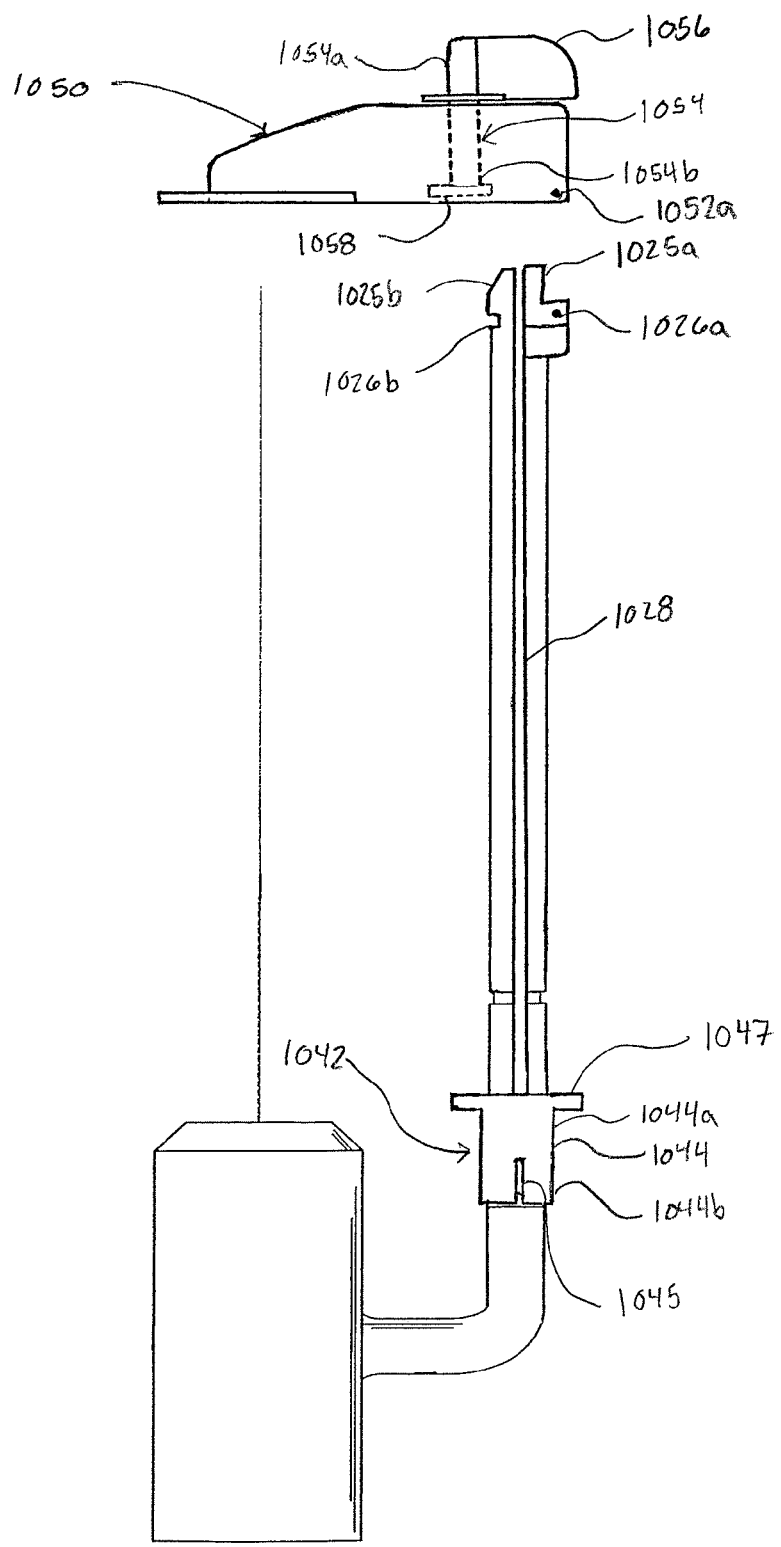
FIG. 34 is a partial cross-sectional elevational view of the tensioning arm of FIG. 33.
Figure 35:
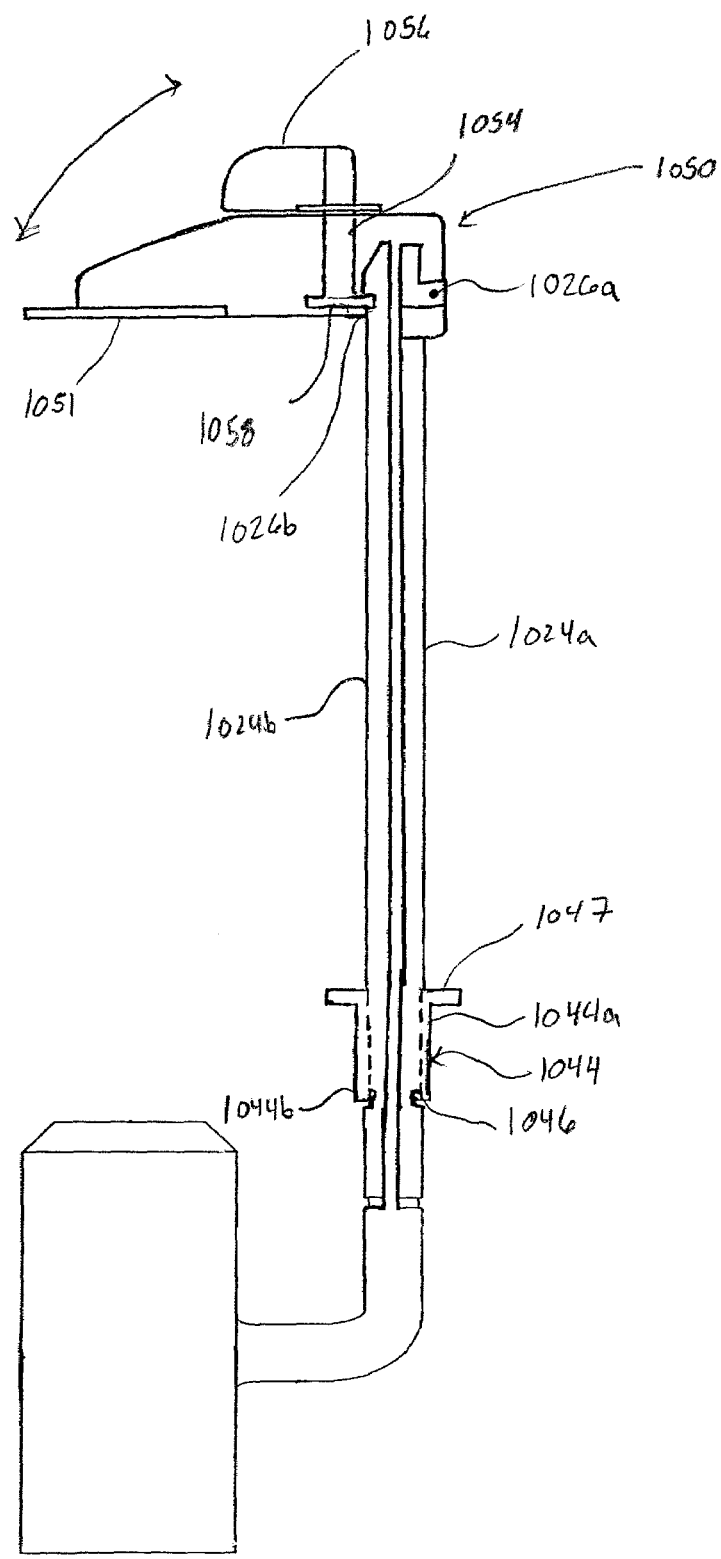
FIG. 35 is an exploded elevational view of the tensioning arm of FIGS. 33-34.

Referring now to FIG. 32, in an alternate embodiment, tensioning member 920 includes a tensioning arm 924 having a pair of parallel spaced apart fingers 924a, 924b forming slot 928 therebetween and defining a distal opening 925 in communication with slot 928. Spaced apart fingers 924a, 924b further define alternating protrusions 929 extending into slot 928. Protrusions 929 are configured such that a bandage "B" may be positioned within slot 928 by sliding bandage "B" into slot 928 through distal opening 925. Protrusions 930 enable bandage "B" to be drawn through slot 928 while maintaining tension on bandage "B". Protrusions 930 may take the form of a cantilevered arcuate member having a first end 930a attached to a respective finger 924a, 924b and a second free end 930b.

In an alternate embodiment, fingers 924a, 924b may necessitate deflection in order to slide bandage "B" through slot 928. In this manner, bandage "B" will be more securely received in slot 928.

In yet another embodiment fingers 924a, 924b may be configured to receive a ring 942 for adjusting the size of slot 928. Ring 924 may be selectively positionable prior to or after bandage "B" has been inserted through slot 928. In an alternate embodiment ring 924 may be configured to deflect fingers 924a, 924b toward one another in order to more securely receive bandage "B" in slot 928.

Turning now to FIGS. 33-36B, in still yet another embodiment, tensioning member 1020 includes a tensioning arm 1024 operatively connected to leg 1026 extending from base 1022. Tensioning arm 1024 includes a pair of substantially parallel spaced apart first and second fingers 1024a, 1024b defining a slot 1028, therebetween. Tensioning arm 1024 further includes an adjustment sleeve 1042 slidable disposed thereon for adjusting the height of slot 1028. Tensioning member 1020 further includes a tensioning mechanism 1050 pivotably secured to the distal end of tensioning arm 1024 for narrowing slot 1028.

As noted above, the height of slot 1028 may be adjusted using adjustment sleeve 1042. By adjusting the height of slot 1028, tensioning member 1020 may accommodate bandages, or the like, of varying heights. Adjustment sleeve 1042 may be configured to be slidably received about tensioning arm 1024. Adjustment sleeve 1042 includes a substantially annular base 1044 having proximal and distal ends 1044a, 1044b, respectively. Proximal end 1044a of annular base 1044 forms a guide surface 1047 for preventing a bandage from slipping below and/or beyond annular base 1044. Distal end 1044b of annular base 1044 is configured to include one or more slots 1045. Distal end 1044b further includes a lip or tab 1046 thereabout. Lip 1046 is configured to be selectively received within at least one of notches 1030 formed in tensioning arm 1024. When lip 1046 is engaged within notch 1030 adjustment sleeve 1042 is prevented from sliding about tensioning arm 1024. Slots 1045 formed in annular base 1044 permit proximal end 1044b thereof to expand thereby causing lip 1046 to disengage from within notch 1030. In this manner adjustment sleeve 1042 may be slidably repositioned about tensioning arm 1024. One or more notches 1030 may be spaced such that slot 1028 may be selectively adjusted for known bandage sizes, or in the alternative, in regularly spaced intervals. Tensioning arm 1024 may further include markings or gradations for assisting in alignment of adjustment sleeve 1042 relative to tensioning arm 1024.

The distal ends 1025a, 1025b of first and second fingers 1024a, 1024b, respectively, are configured to operably engage tensioning mechanism 1050. Distal end 1025a of first finger 1024a includes an opening 126a for pivotably receiving tensioning mechanism 1050. A connection pin or pins (not shown) may be used to pivotably connect tensioning member 1050 with distal end 1025a of first finger 1024a. In the alternative, tensioning mechanism 1050 may be configured to include knobs or protrusions (not shown) for pivotably engaging opening 126a. Distal end 1025b of second finger 1024b is configured to be engageably received within tensioning mechanism 1050. Distal end 1025b of second finger 1024b defines a notch 1026b for selectively receiving a portion of tensioning member 1050, as will be described in detail below.

Tensioning member 1050 includes a base 1052, a rotatable shaft 1054 extending therethrough having first and second ends 1054a, 1054b. Fixedly attached to first end 1054a is lever 1056 for selectively rotating shaft 1054. Second end 1054b of shaft 1054 includes a cam 1058 for selectively engaging notch 1026b defined by distal end 1025b of second finger 1024b, as will be described below. Base 1052 is configured to be received over distal ends 125a, 125b of first and second fingers 1024a, 1024b, respectively. Base 1052 further includes an opening 1052a configured to receive a pin or pins (not shown) for pivotably connecting base 1052 with distal end 1025a of first finger 1024a. In an alternate embodiment, base 1052 of tensioning member 1050 may include tabs or protrusions (not shown) for being pivotably received within opening 1026a formed in distal end 1025a of first finger 1024a.

Figure 36A:
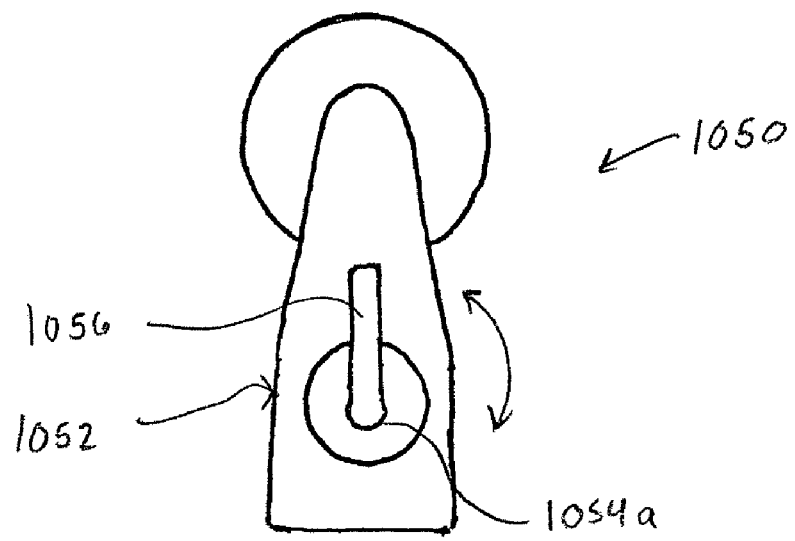
FIG. 36A is a top elevational view of the tensioning mechanism of tensioning arm of FIGS. 33-35.
Figure 36B:
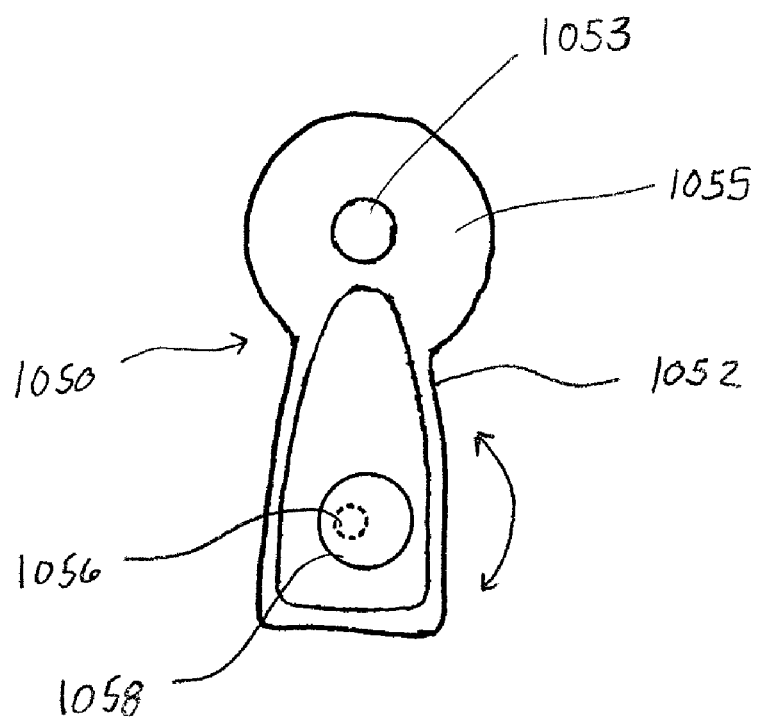
FIG. 36B is a bottom elevational view of the tensioning mechanism of FIGS. 33-36A.

With particular reference to FIGS. 36B, base 1052 of tensioning member 1050 is configured to include an opening 1053 formed on a distal end thereof for receiving a distal end of an above disclosed winding peg. Base 1052 defines a guide surface 1055 formed about opening 1053. Guide surface 1055 is configured to prevent a bandage or the like from extending above or beyond tensioning member 1050. In this manner, guide surface 1055 retains a bandage or the like on the winding peg as it is wound.

Still referring to FIG. 36B, second end 1054b of shaft 1054 forms a cam 1058. Cam 1058 may be offset or axially misaligned from shaft 1054. With additional reference to FIGS. 34 and 35, when lever 1056 is rotated in a first position (FIG. 34) cam 1058 is formed thereon does not engage notch 1026b formed on distal end 1025b of second finger 1024b. As lever 1056 is rotated relative to base 1052 cam 1058 begins to engage notch 1058. Depending on the configuration of cam 1058, notch 1058 may be fully engaged at any point during the rotation. Preferably, cam 1058 is configured such that 180 degrees of rotation cam 1058 causes distal end 1025a, 1025b, of first and second fingers 1024a, 1024b, respectively, to be squeezed towards one another. In this manner, a bandage that has been threaded through slot 1028 of tensioning arm 1024 may be more securely grasped therebetween, thereby maintaining tension on the bandage as it is wound about a winding peg. Cam 1058 further acts to pivotably lock tensioning mechanism 1050 with tensioning arm 1024. Once the bandage has been completely wound about the winding peg, lever 1056 may be rotated to the original first position, thereby disengaging cam 1058 from within notch 1026b and enabling tensioning mechanism 1050 to be pivoted from about distal ends 125a, 125b of first and second fingers 1024a, 1024b, respectively.

Thus, it should be understood that various changes in form, detail and operation of the winding apparatus of the present disclosure may be made without departing from the spirit and scope of the present disclosure.

What is claimed is:

1. A portable, hand held winding apparatus, for rolling up or winding elongate bandages, the winding apparatus comprising:

a hand held rotary drive device having a motor-driven rotatable connector that is adapted to operatively engage a connecting member, the rotatable connector defining an axis of rotation;

a tensioning member supportable on the rotary drive device, the tensioning member including a tensioning arm extending in a direction substantially parallel to the rotational axis of the rotatable connector of the rotary drive device, the tensioning arm defining a slot therein; and a winding peg defining a slot therein and including a connecting member extending axially therefrom, the connecting member being operatively engageable with the rotatable connector of the rotary drive device.

2. The winding apparatus according to claim 1, wherein the slot formed in the tensioning arm includes a closed proximal end and selectively open distal end.

3. The winding apparatus according to claim 1, wherein the tensioning arm includes an endcap pivotally mounted on a distal end thereof.

4. The winding apparatus according to claim 3, wherein the slot formed in the winding peg includes a first and second slot portion, wherein the second slot portion is narrower than the first slot portion.

5. The winding apparatus according to claim 4, wherein the second slot portion has a width of approximately 0.125 inches (31.25 mm).

6. A portable, hand held winding apparatus, for rolling up or winding elongate bandages, the winding apparatus comprising:

a hand held rotary drive device having a motor-driven rotatable connector that is adapted to operatively engage a connecting member, the rotatable connector defining an axis of rotation;

a tensioning member supportable on the rotary drive device, the tensioning member including a tensioning arm extending in a direction substantially parallel to the rotational axis of the rotatable connector of the rotary drive device, the tensioning arm defining a slot therein; and a winding peg including a means for selectively receiving a bandage, the winding peg defining a connecting member extending axially therefrom, the connecting member being operatively engageable with the rotatable connector of the rotary drive device.

7. The portable, hand-held winding apparatus of claim 6, wherein the means for selectively receiving a bandage includes a plurality of fingers.

8. The portable, hand-held winding apparatus of claim 7, wherein the plurality of fingers form a teardrop shape.

9. The portable, hand-held winding apparatus of claim 7, wherein the plurality of fingers form a tweezers configuration.

10. A portable, hand held winding apparatus, for rolling up or winding elongate bandages, the winding apparatus comprising:

a hand held rotary drive device having a motor-driven rotatable connector that is adapted to operatively engage a connecting member, the rotatable connector defining an axis of rotation;

a tensioning member supportable on the rotary drive device, the tensioning member including a tensioning arm extending in a direction substantially parallel to the rotational axis of the rotatable connector of the rotary drive device, the tensioning arm defining a slot therein; and a winding peg having proximal and distal ends, the proximal end defining a connecting member extending axially therefrom, the connecting member being securely engaged with the rotatable connector of the rotary drive device, the distal end defining a means for selectively receiving a bandage.

11. The portable, hand-held winding apparatus of claim 10, wherein the means for selectively receiving a bandage is a clip.

12. The portable, hand-held winding apparatus of claim 11, wherein the clip is fixedly attached to the proximal end of the winding peg.

13. The portable, hand-held winding apparatus of claim 11, wherein the clip is fixedly attached to the distal end of the distal end winding peg.

14. A portable, hand held winding apparatus, for rolling up or winding elongate bandages, the winding apparatus comprising:
   a hand held rotary drive device having a motor-driven rotatable connector that is adapted to operatively engage a connecting member, the rotatable connector defining an axis of rotation;
   a tensioning member supportable on the rotary drive device, the tensioning member including a tensioning arm extending in a direction substantially parallel to the rotational axis of the rotatable connector of the rotary drive device, the tensioning arm defining a slot therein, the tensioning member further including a drag bar mounted parallel to the tensioning arm; and
   a winding peg defining a slot therein and including a connecting member extending axially therefrom, the connecting member being operatively engageable with the rotatable connector of the rotary drive device.

15. A portable, hand held winding apparatus, for rolling up or winding elongate bandages, the winding apparatus comprising:
   a hand held rotary drive device having a motor-driven rotatable connector that is adapted to operatively engage a connecting member, the rotatable connector defining an axis of rotation;
   a tensioning member supportable on the rotary drive device, the tensioning member including a tensioning arm extending in a direction substantially parallel to the rotational axis of the rotatable connector of the rotary drive device, the tensioning arm defining a slot therein configured for receiving a bandage, wherein the tensioning arm includes protrusions extending into the slot thereof; and
   a winding peg defining a slot therein and including a connecting member extending axially therefrom, the connecting member being operatively engageable with the rotatable connector of the rotary drive device.

16. The portable, hand-held winding apparatus of claim 15, wherein the protrusions are aligned.

17. The portable, hand-held winding apparatus of claim 15, wherein the protrusions are alternately spaced.

18. The portable, hand-held winding apparatus of claim 15, wherein the slot of the tensioning arm has an open distal end.

19. The portable, hand-held winding apparatus of claim 15, wherein the protrusions extend toward one another from opposed surfaces of the slot of the tensioning arm.

20. A portable, hand held winding apparatus, for rolling up or winding elongate bandages, the winding apparatus comprising:
   a hand held rotary drive device having a motor-driven rotatable connector that is adapted to operatively engage a connecting member, the rotatable connector defining an axis of rotation;
   a tensioning member supportable on the rotary drive device, the tensioning member including a tensioning arm extending in a direction substantially parallel to the rotational axis of the rotatable connector of the rotary drive device, the tensioning arm defining an adjustable slot therein; and
   a winding peg defining a slot therein and including a connecting member extending axially therefrom, the connecting member being operatively engageable with the rotatable connector of the rotary drive device.

21. The portable, hand held winding apparatus of claim 20, wherein the slot defined by the tensioning arm includes a selectively variable height.

22. The portable, hand held winding apparatus of claim 20, wherein the slot defined by the tensioning arm includes a selectively variable width.

23. The portable, hand held winding apparatus of claim 20, wherein the tensioning member further includes a tensioning mechanism.

24. The portable, hand held winding apparatus of claim 23, wherein the tensioning mechanism is pivotably mounted to the distal end of the tensioning member.

* * * * *